US011649198B2

(12) United States Patent
Weaver et al.

(10) Patent No.: US 11,649,198 B2
(45) Date of Patent: *May 16, 2023

(54) CONVERSION OF ETHANE TO ETHYLENE

(71) Applicant: University of Florida Research Foundation, Inc., Gainesville, FL (US)

(72) Inventors: Jason F. Weaver, Gainesville, FL (US); Yingxue Bian, Golden, CO (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/528,675

(22) Filed: Nov. 17, 2021

(65) Prior Publication Data
US 2022/0073439 A1   Mar. 10, 2022

Related U.S. Application Data

(63) Continuation of application No. 16/959,325, filed as application No. PCT/US2019/014114 on Jan. 18, 2019, now Pat. No. 11,208,366.

(60) Provisional application No. 62/747,359, filed on Oct. 18, 2018, provisional application No. 62/618,813, filed on Jan. 18, 2018.

(51) Int. Cl.
*C07C 5/333* (2006.01)
*B01J 23/46* (2006.01)
*C07C 11/04* (2006.01)

(52) U.S. Cl.
CPC .......... *C07C 5/3337* (2013.01); *B01J 23/468* (2013.01); *C07C 11/04* (2013.01); *C07C 2523/46* (2013.01)

(58) Field of Classification Search
None
See application file for complete search history.

(56) References Cited

U.S. PATENT DOCUMENTS

| 3,830,868 A | 8/1974 | Walker |
| 2012/0083637 A1 | 4/2012 | Clem et al. |
| 2019/0126242 A1 | 5/2019 | Xing et al. |

OTHER PUBLICATIONS

Bian, Yingxue, et al., "Facile Dehydrogenation of Ethane on the IrO2 (110) Surface," Journal of the American Chemical Society, 2018, pp. 2665-2672, vol. 140, ACS Publications, doi: 10.1021/jacs.7b13599.
"Iridium(IV) oxide," Wikipedia, https://en.wil<ipedia.org/w/index.php?title=Iridium(IV)_oxide&oldid=808690822 (accessed Mar. 22, 2019).
Pham, T. L. M., E.G. Leggesse, and J.C. Jiang, "Ethylene formation by methane dehydrogenation and C—C coupling reaction on a stoichiometric IrO2 (110) surface—a density functional theory investigation," Catalysis Science & Technology, 2015, pp. 4064-4071, vol. 5, doi: 10.1039/c5cy00118h.
Jiang et al., "A DFT study of ethane activation on IrO2(110) surface by precursor-mediated mechanism," Applied Catalysis A, General, Elsevier B.V.(Jan. 6, 2017).

*Primary Examiner* — Philip Y Louie
(74) *Attorney, Agent, or Firm* — Thomas|Horstemeyer, LLP

(57) ABSTRACT

Methods of converting ethane to ethylene at relatively low temperatures are described. $IrO_2$-based catalysts are used in the conversion. Methods of converting a base gas to a first gas by exposing the base gas to an $IrO_2$-based catalyst and forming the first gas are described. The base gas can be an alkane. The first gas can include an alkene, an alkyne, an alcohol, an aldehyde, or combinations thereof.

19 Claims, 10 Drawing Sheets

CONVERSION OF ETHANE TO ETHYLENE

CLAIM OF PRIORITY TO RELATED APPLICATION

This application is a continuation of U.S. application entitled "Conversion of Ethane to Ethylene" having Ser. No. 16/959,325 filed on Jun. 30, 2020, which application is the 35 U.S.C. § 371 national stage of PCT application having serial number PCT/US2019/014114, filed on Jan. 18, 2019. The PCT application also claims the benefit of and priority to U.S. Provisional Application Ser. No. 62/747,359, having the title "CONVERSION OF ETHANE TO ETHYLENE", filed on Oct. 18, 2018, and further claims the benefit of and priority to U.S. Provisional Application Ser. No. 62/618,813, having the title "CONVERSION OF ETHANE TO ETHYLENE", filed on Jan. 18, 2018 the disclosure of each of which is incorporated herein by reference in their entireties.

GOVERNMENT FUNDING

This invention was made with Government support under DE-FG02-03ER15478 awarded by the Department of Energy. The Government has certain rights in this invention.

BACKGROUND

Developing catalysts that can directly convert ethane to ethylene is gaining increasing interest due to the availability of light alkanes from shale gas as well as the increasing demand for ethylene. However, the catalysts that have been investigated to date do not achieve sufficient activity and selectivity to be utilized at the industrial scale.

SUMMARY

Embodiments of the present disclosure provide for methods of converting a base gas to a first gas by exposing the base gas to an $IrO_2$-based catalyst and forming the first gas. The base gas can be an alkane. The first gas can include an alkene, an alkyne, an alcohol, an aldehyde, or combinations thereof.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1B:
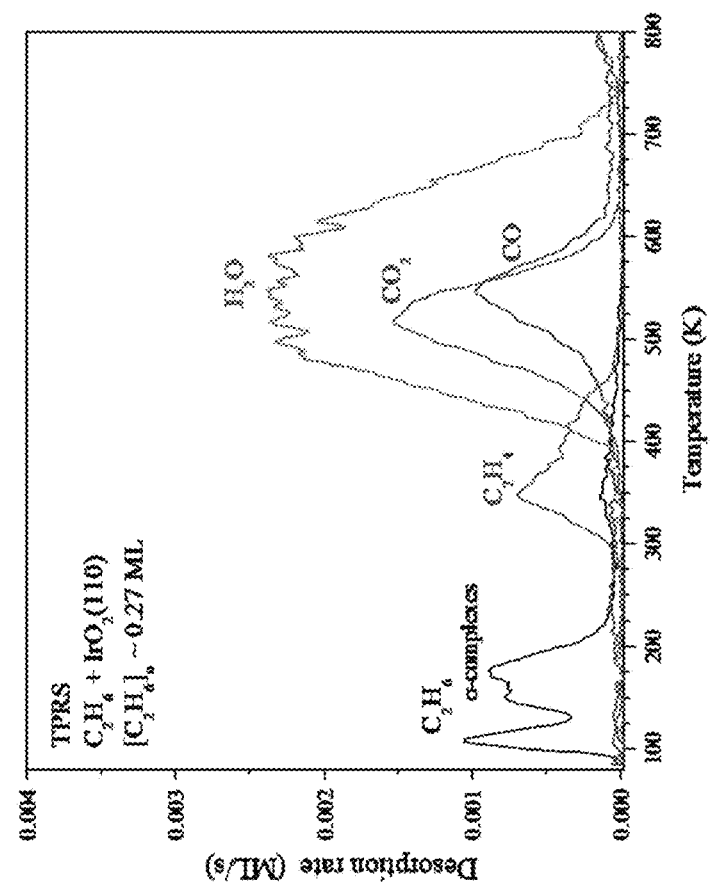
FIGS. 1A-1B provide examples of TPRS spectra of $C_2H_6$, $C_2H_4$, CO, $CO_2$ and $H_2O$ obtained after adsorbing $C_2H_6$ on $IrO_2(110)$ at 90 K to reach initial $C_2H_6$ coverages of (FIG. 1A) 0.11 ML and (FIG. 1B) 0.27 ML.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, "alkane" refers to a saturated aliphatic hydrocarbon which can be straight or branched, having 1 to 40, 1 to 20, 1 to 10, or 1 to 5 carbon atoms, where the stated range of carbon atoms includes each intervening integer individually, as well as sub-ranges. Examples of alkane include, but are not limited to methane, ethane, propane, butane, pentane, and the like. Reference to "alkane" includes unsubstituted and substituted forms of the hydrocarbon.

As used herein, "alkyne" refers to straight or branched chain hydrocarbon groups having 2 to 40, 2 to 20, 2 to 10, or 2 to 5 carbon atoms and at least one triple carbon to carbon bond. Reference to "alkyne" includes unsubstituted and substituted forms of the hydrocarbon. As used herein, "alkene" refers to an aliphatic hydrocarbon which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkene groups include, but are not limited to, ethene, propene, and the like.

As used herein, "alcohol" refers to a R—OH, where R can be alkyl group. An alkyl group refers to a straight or branched moiety, having 1 to 40, 1 to 20, 1 to 10, or 1 to 5 carbon atoms, where the stated range of carbon atoms includes each intervening integer individually, as well as sub-ranges. Examples of alcohol include, but are not limited to methanol, ethanol, propanol, butane, pentanol, and the like. Reference to "alcohol" includes unsubstituted and substituted forms of the alcohol.

As used herein, "aldehyde" refers to a R(O)H, where R can be alkyl group. An alkyl group refers to a straight or branched moiety, having 1 to 40, 1 to 20, 1 to 10, or 1 to 5 carbon atoms, where the stated range of carbon atoms includes each intervening integer individually, as well as sub-ranges. Examples of aldehyde include, but are not limited to formaldehyde, acetaldehyde, propionaldehyde, butyraldehyde, and the like. Reference to "aldehyde" includes unsubstituted and substituted forms of the aldehyde.

Discussion

Embodiments of the present disclosure provide for methods of converting alkanes (e.g., ethane) to a first gas (e.g., an alkene, an alkyne, an alcohol, an aldehyde, or a combination thereof), systems, catalysts, and the like.

Current industrial practice is to use the so-called steam-cracking process to produce ethylene from ethane. In the steam-cracking process, the ethane reactant is diluted in steam and heated to high temperature (~800° C.) to promote ethane pyrolysis. Steam-cracking is highly energy intensive and produces large quantities of CO and $CO_2$ as byproducts. Equipment costs and maintenance are also substantial. A catalytic process that can efficiently and selectively convert ethane to ethylene at lower temperature would have significant economic and environmental benefits.

Developing efficient methods for directly converting ethane to ethylene has gained increasing interest due to the availability of shale gas and the increasing demand for ethylene. Ethylene is produced and sold in the largest quantities among all products generated by the petrochemical industry. Realizing the efficient and selective conversion of ethane to ethylene is important for improving the utilization of hydrocarbon resources, yet remains a major challenge in catalysis. Catalysts that have been investigated to date are not sufficiently efficient and selective to be put into industrial practice for converting ethane to ethylene. The methods described in the present disclosure provide more efficient alternatives for generating ethylene from ethane.

Embodiments of the present disclosure provide for methods of converting a base gas to a first gas. The method includes exposing the base gas to an $IrO_2$-based catalyst and forming the first gas. The base gas can include a C1 to C8, or C1 to C6, or C1 to C5, or C1 to C4 alkane. In an example, the alkane can be methane, ethane, propane, and combinations thereof. For example, the base gas may be natural gas. The first gas can include a C1 to C8, or C1 to C6, or C1 to C5, or C1 to C4 alkene, a C1 to C8, or C1 to C6, or C1 to C5, or C1 to C4 alkyne, a C1 to C8, or C1 to C6, or C1 to C5, or C1 to C4 alcohol, a C1 to C8, or C1 to C6, or C1 to C5, or C1 to C4 aldehyde, or a combination thereof. In various embodiments, the base gas can be ethane or methane, while the first gas can include ethylene, methanol, formaldehyde, or combinations thereof.

In some embodiments, the $IrO_2$-based catalyst can be partially hydrogenated (e.g. can be pre-hydrogenated prior to exposure to the base gas). In various embodiments, the $IrO_2$-based catalyst can be $IrO_2(110)$.

In an aspect, it was found that ethane forms strongly-bound sigma-complexes on the $IrO_2(110)$ surface and that a large fraction of the complexes undergo C—H bond cleavage at temperatures below 200 K during temperature programmed reaction spectroscopy (TPRS) experiments. It was found that continued heating causes as much as 40% of the dissociated ethane to dehydrogenate and desorb as ethylene near 350 K, with the remainder oxidizing to CO and $CO_2$. It was also determined that partial hydrogenation of the $IrO_2$(110) surface enhances ethylene production from ethane while suppressing oxidation to $CO_x$ species. These experiments reveal that $IrO_2$(110) exhibits an exceptional ability to promote ethane dehydrogenation to ethylene just above room temperature, and demonstrate that controlled prehydrogenation of the $IrO_2$(110) surface is an effective approach for increasing selectivity toward ethane conversion to ethylene rather than CO and $CO_2$.

Prehydrogenation, as described herein, is attained via the following process. First, $H_2$ is adsorbed on the $IrO_2$(110) surface at 90 K and then heated to 380 K. The $H_2$ exposure to the surface can be varied to control the H surface concentration. Heating to 380 K has two effects: it increases the quantity of surface OH groups and also causes H atoms to vacate the Ir sites needed for alkane adsorption and activation. The $H_2$ dissociation process may be represented as $H_2$—Ir+0 to H-Ir+OH. Heating causes the following: H-Ir+0 to Ir+OH Lastly, the temperature is limited to 380 K to avoid reduction of the surface via 2OH to $H_2O$(g). The precise adsorption temperature (90 K) is not critical and neither is heating. However, the heating step helps achieve a more desirable surface in which a large fraction of Ir atoms are vacant and the majority of the surface H-atoms are bound to O-atoms, giving OH groups.

In various embodiments, the base gas (such as an alkane) can be exposed to an $IrO_2$-based catalyst at a temperature of about 90 to 500 K, about 200 to 400 K, or about 350 K. Our work shows that the $IrO_2$(110) surface activates ethane C—H bonds at temperatures below 200 K, and that a large portion of the dissociated ethane dehydrogenates and desorbs as ethylene at temperatures of about 300 to 450 K. Selectivity toward ethylene production during TPRS increases with increasing initial ethane coverage. No other material is capable of achieving ethane to ethylene conversion at these low temperatures and with the efficiency realized on $IrO_2$(110). The discovery of this efficient chemical transformation has potential to serve as the basis for developing $IrO_2$-based catalysts that can directly and efficiently promote the conversion of ethane to ethylene. The successful development of such a process for industrial application would have transformative impact on the commercial production of ethylene. The economic benefits could be enormous.

Nearly 40% of the adsorbed ethane converts to ethylene during TPRS when the ethane layer is initially saturated.

DFT calculations confirm that "bridging" HO groups of the $IrO_2$(110) surface are effectively inactive as H-atom acceptors, and that conversion of surface bridging-O atoms to HO groups hinders extensive dehydrogenation of adsorbed ethane-derived species and promotes ethylene desorption.

Polycrystalline and nanoparticle forms of $IrO_2$ and $IrO_2$ surface facets will promote facile ethane dehydrogenation and conversion to ethylene. This discovery demonstrates that pairs of coordinatively unsaturated (cus) Ir and O atoms at the surface are needed to achieve the observed reactivity on $IrO_2$(110). Such sites are present on the surface of other forms of $IrO_2$.

In some embodiments, the $IrO_2$-based catalyst can have the formula $Ir_xM_yO_z$, where M is selected from Ru, Ti, Re, Nb, Ta, Os, Pt, Pd, Cu, Ag, Au, Rh, Cr, Mn, Ni, Fe, Co or a combination thereof, and where z is between 1 and 2 and x+y≤1. Mixed oxides that include $IrO_2$ moieties will promote facile ethane dehydrogenation and conversion to ethylene, including solid oxide solutions in which Ir atoms and a second metal cation (M) are present on separate cation lattice sites of the oxide structure in a range of compositions.

In some embodiments, the $IrO_2$ based catalyst can have the formula $Ir_xO_yX_z$, where X is selected from F, Cl, Br, I, S, Se, Te, or a combination thereof, wherein x≤1 and y+z is between 1 and 2. $IrO_2$ deposited onto another metal oxide (e.g. $SiO_2$, $Al_2O_3$, $TiO_2$, MgO, CaO, $CeO_2$, zeolites or a combination thereof), referred to as a support oxide, or various non-oxide support materials (e.g. carbon) will promote facile ethane dehydrogenation and conversion to ethylene. Anion-substituted, solid mixtures of the form $Ir_xO_yX_z$ will promote facile ethane dehydrogenation and conversion to ethylene, where X represents an element that replaces a fraction of the O-atoms in the anion sub-lattice.

Various forms of $IrO_2$, as listed above, are able to promote the selective dehydrogenation and oxidation of methane to desirable organic products, including but not limited to ethylene, methanol and formaldehyde.

Various forms of $IrO_2$, as listed above, are able to promote the selective dehydrogenation and oxidation of higher alkanes in pure form and mixtures to generate desirable organic products, including but not limited to alkenes, alkynes, alcohols, aldehydes and other value-added species (e.g., ketones, esters, ethers and organic acids).

Various forms of $IrO_2$, as listed above, can promote the steady-state, selective dehydrogenation and oxidation of alkanes, including methane, ethane and higher alkanes, to value-added products. Mixtures of the alkane(s) of interest and $O_2$ can be continuously fed to a reactor containing the $IrO_2$-based catalyst, and continuously produce value-added products.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Realizing the efficient and selective conversion of ethane to ethylene is important for improving the utilization of hydrocarbon resources, yet remains a major challenge in catalysis. Herein, ethane dehydrogenation on the $IrO_2$(110) surface is investigated using temperature programmed reaction spectroscopy (TPRS) and density functional theory (DFT) calculations. The results show that ethane forms strongly-bound σ-complexes on $IrO_2$(110) and that a large fraction of the complexes undergo C—H bond cleavage during TPRS at temperatures below 200 K. Continued heating causes as much as 40% of the dissociated ethane to dehydrogenate and desorb as ethylene near 350 K, with the remainder oxidizing to $CO_x$ species. Both TPRS and DFT show that ethylene desorption is the rate-controlling step in the conversion of ethane to ethylene on $IrO_2$(110) during TPRS. Partial hydrogenation of the $IrO_2$(110) surface is found to enhance ethylene production from ethane while suppressing oxidation to $CO_x$ species. DFT predicts that hydrogenation of reactive oxygen atoms of the $IrO_2$(110) surface effectively deactivates these sites as H-atom acceptors, and causes ethylene desorption to become favored over further dehydrogenation and oxidation of ethane-derived species. The study reveals that $IrO_2$(110) exhibits an exceptional ability to promote ethane dehydrogenation to ethylene near room temperature, and provides molecular-level insights for understanding how surface properties influence selectivity toward ethylene production.

Introduction

Developing catalysts that can directly convert ethane to ethylene is gaining increasing interest due to the availability of light alkanes from shale gas as well as the increasing demand for ethylene. The oxidative dehydrogenation (ODH) of ethane offers advantages over non-oxidative processes and has been widely studied.[1-3] The ODH of ethane occurs in the presence of oxygen and involves the dehydrogenation of ethane to ethylene with concurrent oxidation of the released hydrogen to water. The latter step makes the ODH of ethane an exothermic process for which high conversion is thermodynamically favored at low temperature. Furthermore, the presence of oxygen in the reactant stream minimizes catalyst deactivation by coking which can be a significant problem in non-oxidative routes for ethane dehydrogenation. Various metal oxides as well as alkali chlorides are effective in promoting the ODH of ethane and propane, with $VO_x$-based catalysts generally exhibiting the most favorable performance.[1-9] However, the catalysts that have been investigated to date do not achieve sufficient activity and selectivity to be utilized at the industrial scale.

Initial C—H bond cleavage is widely accepted as the rate-controlling step in the ODH of ethane, and more generally in the catalytic processing of light alkanes.[1] This situation presents a challenge in developing catalysts that can selectively dehydrogenate ethane to ethylene because the reaction steps that follow initial C—H bond cleavage occur rapidly and can be difficult to control, particularly in the presence of oxygen. Recently, we have reported that $CH_4$ undergoes highly facile C—H bond activation on the $IrO_2$(110) surface at temperatures as low as 150 K.[10] We find that methane adsorbs as a strongly-bound σ-complex on $IrO_2$(110) and that C—H bond cleavage occurs by a heterolytic pathway wherein the adsorbed complex transfers a H-atom to a lattice oxygen atom, thus affording adsorbed $CH_3$ and OH groups. Our results further show that the resulting methyl groups react with the $IrO_2$(110) surface via oxidation to $CO_x$ and $H_2O$ as well as recombination with adsorbed hydrogen to regenerate $CH_4$, with these products desorbing at temperatures above ~400 K during temperature programmed reaction spectroscopy (TPRS) experiments.[10] Key findings are that the initial C—H bond cleavage of $CH_4$ is highly facile and that subsequent reaction steps control the overall chemical transformations of methane on the $IrO_2$(110) surface. The ability of $IrO_2$(110) to activate alkane C—H bonds at low temperature may provide opportunities to develop catalysts that are capable of directly and efficiently transforming light alkanes to value-added products.

In the present example, we investigated the dehydrogenation of ethane on the $IrO_2$(110) surface. We find that initial C—H bond cleavage of $C_2H_6$ occurs efficiently on $IrO_2$(110) at low temperature (~150 to 200 K) and that subsequent reaction produces $C_2H_4$ as well as $CO_x$ species during TPRS, with the $C_2H_4$ product desorbing between 300 and 450 K. We demonstrate that partially hydrogenating the $IrO_2$(110) surface to convert a fraction of the surface O-atoms to OH groups enhances the conversion of $C_2H_6$ to $C_2H_4$ while suppressing extensive oxidation to $CO_x$ species. Our findings show that the controlled deactivation of surface O-atoms is an effective means for promoting the selective conversion of ethane to ethylene on $IrO_2$(110) at low temperature.

Experimental Details

Details of the ultrahigh vacuum (UHV) analysis chamber with an isolatable ambient-pressure reaction cell utilized in the present study have been reported previously.[10] Briefly, the Ir(100) crystal employed in this study is a circular disk (9 mm×1 mm) that is attached to a liquid-nitrogen-cooled, copper sample holder by 0.015" W wires that are secured to the edge of crystal. A type K thermocouple was spot welded to the backside of the crystal for temperature measurements. Resistive heating, controlled using a PID controller that varies the output of a programmable DC power supply, supports linearly ramping from 80 to 1500 K and maintaining the sample temperature. Sample cleaning consisted of cycles of $Ar^+$ sputtering (2000 eV, 15 mA) at 1000 K, followed by annealing at 1500 K for several minutes. The sample was subsequently exposed to $5 \times 10^{-7}$ Torr of $O_2$ at 900 K for several minutes to remove surface carbon, followed by flashing to 1500 K to remove final traces of oxygen.

We generated an $IrO_2$(110) film by exposing Ir(100) to 5 Torr of $O_2$ (Airgas, 99.999%) for a duration of 10 minutes ($3 \times 10^9$ Langmuir) in the ambient-pressure reaction cell at a surface temperature of 765 K. Our ambient-pressure reaction cell is designed to reach elevated gas pressure while maintaining UHV in the analysis chamber.[10] After preparation of the oxide film, we lowered the surface temperature to 600 K, and then evacuated $O_2$ from the reaction cell and transferred the sample back to the UHV analysis chamber. We exposed the film to ~23 L $O_2$ while cycling the surface temperature between 300 and 650 K to fill oxygen vacancies that may be created during sample transfer from the reaction cell to the analysis chamber. This procedure produces a high-quality $IrO_2$(110) surface that has a stoichiometric surface termination, contains ~40 ML of oxygen atoms and is about 3.2 nm thick.[10-11]

The stoichiometric $IrO_2$(110) surface consists of parallel rows of fivefold coordinated Ir atoms and so-called bridging O atoms, each of which lacks a bonding partner relative to the bulk and is thus coordinatively unsaturated (cus). Hereafter, we refer to the fivefold coordinated Ir atoms as $Ir_{cus}$ atoms and the bridging O-atoms as $O_{br}$ atoms. On the basis of the $IrO_2$(110) unit cell, the areal density of $Ir_{cus}$ atoms and $O_{br}$ atoms is equal to 37% of the Ir(100) surface atom density of $1.36 \times 10^{15}$ $cm^{-2}$. Since $Ir_{cus}$ atoms are active adsorption sites, we define 1 ML as equal to the density of $Ir_{cus}$ atoms on the $IrO_2$(110) surface.

We studied the adsorption of $C_2H_6$ (Matheson, 99.999%) on clean and hydrogen pre-covered $IrO_2$(110) using TPRS. We delivered ethane to the sample from a calibrated beam doser at an incident flux of approximately 0.0064 ML/s with the sample-to-doser distance set to about 15 mm to ensure uniform impingement of ethane across the sample surface. We prepared hydrogen pre-covered $IrO_2$(110) by exposing the surface to varying quantities of $H_2$ at 90 K, followed by heating to 380 K. We have recently reported that this procedure enhances the concentration of $HO_{br}$ groups by promoting the hopping of H-atoms on $Ir_{cus}$ sites to $O_{br}$.[11] We estimate that ~0.075 to 0.15 ML of $H_2$ adsorbs from the vacuum background during cooling of the initially clean $IrO_2$(110) surface, prior to a TPRS experiment. We collected TPRS spectra after ethane exposures by positioning the sample in front of a shielded mass spectrometer at a distance of about 5 mm and then heating at a constant rate of 1 K/s until the sample temperature reached 800 K. To ensure consistency in the composition and structure of the $IrO_2$(110) layer, the surface was exposed to 23.3 L of $O_2$ supplied through a tube doser while cycling the surface temperature between 300 and 650 K after each TPRS experiment. Initially, we monitored a wide range of desorbing species to identify the main products that are generated from reactions of ethane on $IrO_2$(110), and found that the only desorbing species are $C_2H_6$, CO, $CO_2$, $C_2H_4$, $CH_4$ and $H_2O$. We quantified desorption yields using established procedures as described in the SI.

Computational Details

All plane wave DFT calculations were performed using the projector augmented wave pseudopotentials[12] provided in the Vienna ab initio simulation package (VASP).[13-14] The Perdew-Burke-Ernzerhof (PBE) exchange-correlation functional was used with a plane wave expansion cutoff of 450 eV. Dispersion interactions are modeled using the DFT-D3 method developed by Grimme et al.[16] We find that this method provides accurate estimates of the adsorption energies of n-alkanes on PdO(101)[17] and $RuO_2$(110)[18] in comparison with TPD-derived values; however, the DFT-D3 calculations overestimate the adsorption energy of methane on $IrO_2$(110).[10] We find that DFT-D3 calculations using the PBE functional also overestimate the binding energies of $C_2H_4$ and $C_2H_6$ on $IrO_2$(110). We compare the results of DFT-PBE calculations performed with and without dispersion corrections in Table 1, and note that the predictions from both methods support the conclusions of this study. We employed four layers to model the $IrO_2$(110) film, resulting in an ~12 Å thick slab with an additional 25 Å vacuum to avoid spurious interactions normal to the surface. The PBE bulk lattice constant of $IrO_2$ (a=4.54 Å and c=3.19 Å) is used to fix the lateral dimensions of the slab. The bottom two layers are fixed, but all other lattice atoms are allowed to relax during the calculations until the forces are less than 0.05 eV/Å. A 2×4 unit cell with a corresponding 2×2×1 Monkhorst-Pack k-point mesh is used. In the present study, we define the binding energy, $E_b$, of an adsorbed $C_2H_6$ molecule on the surface using the expression, $$E_b = (E_{C_2H_6} + E_{surf}) - E_{C_2H_6/surf}$$

where $E_{C_2H_6/surf}$ is the energy of the state containing the adsorbed $C_2H_6$ molecule, $E_{surf}$ is the energy of the bare surface, and $E_{C_2H_6}$ is the energy of an isolated $C_2H_6$ molecule in the gas phase. All reported binding energies are corrected for zero-point vibrational energy. From the equation above, a large positive value for the binding energy indicates a high stability of the adsorbed $C_2H_6$ molecule under consideration. We evaluated the barriers for $C_2H_6$ dehydrogenation on the $IrO_2$(110) surface using the climbing nudged elastic band (cNEB) method.[19] Our DFT calculations were performed for a single $C_2H_6$ molecule adsorbed within the 2×4 surface model of $IrO_2$(110), and corresponds to an $C_2H_6$ coverage equal to 12.5% of the total density of $Ir_{cus}$ atoms and 25% of the $Ir_{cus}$ density within one $Ir_{cus}$ row.

Results and Discussion

TPRS of $C_2H_6$ Adsorbed on $IrO_2$(110)

Figure 1A:
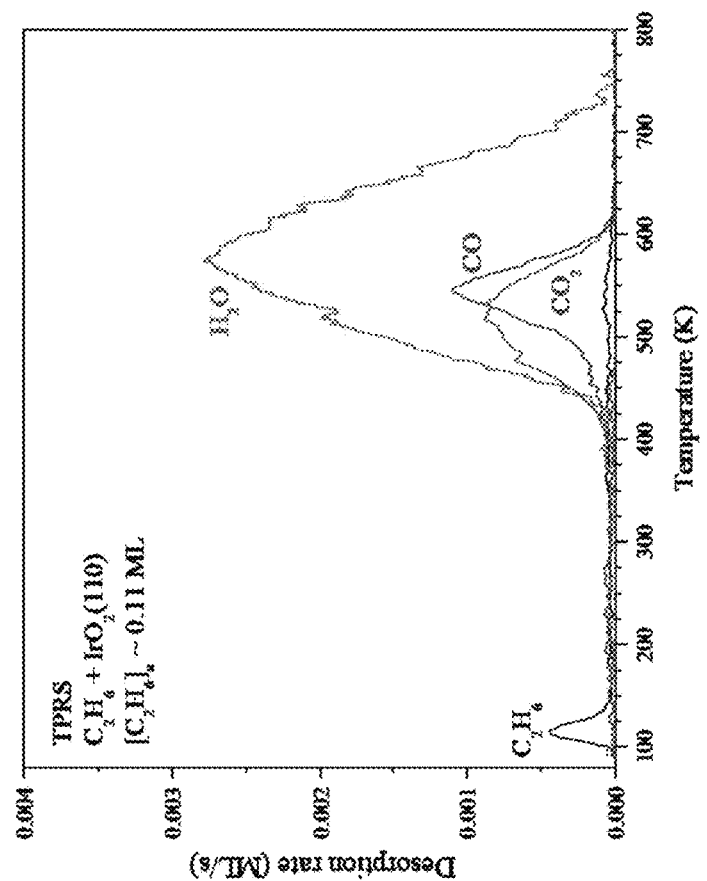

Our TPRS results show that the $IrO_2$(110) surface is highly reactive toward ethane as more than 90% of the $C_2H_6$ adsorbed on $IrO_2$(110) oxidizes to CO, $CO_2$ and $H_2O$ during TPRS at low initial $C_2H_6$ coverages (FIG. 1A). The $CO_2$ and CO products desorb in TPRS peaks centered at 525 and 550 K, while $H_2O$ desorbs over a broader feature spanning temperatures from ~400 to 750 K. We also observe a small $C_2H_6$ TPRS peak at 110 K that arises from weakly-bound, molecularly-adsorbed $C_2H_6$, likely associated with a minority surface phase.

At high initial $C_2H_6$ coverages, a fraction of the adsorbed $C_2H_6$ dehydrogenates to produce $C_2H_4$ in addition to undergoing extensive oxidation to CO and $CO_2$ (FIG. 1b). Ethylene desorption accounts for about 38% of the total amount of $C_2H_6$ that reacts during TPRS at saturation of the initial $C_2H_6$ layer. The $C_2H_4$ TPRS feature resulting from $C_2H_6$ dehydrogenation on $IrO_2$(110) exhibits a maximum at 350 K and a shoulder centered at ~425 K, and most of the $C_2H_4$ desorbs at lower temperature than the CO and $CO_2$ products. Assuming maximum values of the desorption pre-factors ($5.6 \times 10^{18}$, $1.1 \times 10^{19}$ s$^{-1}$), we estimate that the $C_2H_4$ peak temperatures of 350 and 425 K correspond to $C_2H_4$ binding energies of 132 and 162 kJ/mol, respectively. Prior studies show that maximum desorption pre-factors are appropriate for describing the desorption of small hydrocarbons from $TiO_2$(110) and $RuO_2$(110) surfaces,[18, 20] where the pre-factors are computed using a model based on transition state theory.[21] We have performed TPRS experiments following $C_2H_4$ adsorption on $IrO_2$(110), and find that $C_2H_4$ desorbs in a broad feature spanning temperatures from ~150 to 500 K. The breadth of this TPRS feature likely reflects a sensitivity of the $C_2H_4$ binding energy and configuration(s) to the local environment. Because the $C_2H_4$ TPRS feature resulting from $C_2H_6$ dehydrogenation desorbs over a similar temperature range as $C_2H_4$ adsorbed on $IrO_2$(110), we conclude that $C_2H_4$ production from $C_2H_6$ on $IrO_2$(110) is a desorption-limited process.

A new $C_2H_6$ TPRS feature centered at 185 K emerges after the TPRS features generated by the CO, $CO_2$, $C_2H_4$, $H_2O$ products first saturate at a total $C_2H_6$ coverage near 0.20 ML (SI), with this TPRS feature developing two maxima at ~150 and 175 K as its desorption yield begins to saturate (FIG. 1B). The $C_2H_6$ TPRS peak at 110 K grows only slowly as the total $C_2H_6$ coverage increases to about 0.35 ML, but a separate peak at 120 K intensifies sharply thereafter (FIG. 6). The $C_2H_6$ TPRS feature at 150-185 K is consistent with the desorption of relatively strongly-bound $C_2H_6$ σ-complexes adsorbed on the $Ir_{cus}$ atoms of $IrO_2$(110). Using Redhead analysis with a maximum value of the desorption pre-factor ($5.9 \times 10^{17}$ s$^{-1}$), we predict a binding energy of 65 kJ/mol for the $C_2H_6$ TPRS peak at 185 K. We also estimate a saturation coverage of ~0.30 ML for $C_2H_6$ σ-complexes on $IrO_2$(110), based on the amount of $C_2H_6$ that desorbs above ~135 K plus the total amount that reacts. Our estimate agrees to within about 20% of the saturation coverage of $C_2H_6$ σ-complexes on $RuO_2$(110).[18] Because the σ-complexes serve as dissociation precursors (see below), our TPRS results reveal that $C_2H_6$ C—H bond cleavage occurs readily on $IrO_2$(110) at temperatures between ~150 and 200 K, i.e., in the same range as desorption of the $C_2H_6$ σ-complexes. We are unaware of other materials that exhibit such high activity toward promoting the C—H bond activation of $C_2H_6$.

We have recently shown that $IrO_2$(110) is exceptionally active in promoting $CH_4$ C—H bond cleavage at temperatures as low as 150 K.[10] The present results demonstrate a similarly high reactivity of $IrO_2$(110) toward $C_2H_6$ activation. Our prior study shows that $CH_4$ initially adsorbs on $Ir_{cus}$ atoms and undergoes C—H bond cleavage by a heterolytic pathway involving H-atom transfer to a neighboring $O_{br}$ atom, producing $CH_3$—$Ir_{cus}$ and $HO_{br}$ groups. We found that the energy barrier for $CH_4$ bond cleavage is nearly 10 kJ/mol lower than the binding energy of the $CH_4$ σ-complex, resulting in near unit dissociation probability for $CH_4$ on $IrO_2$(110) at low temperature and coverage. The resulting $CH_3$ groups are oxidized by the surface to CO, $CO_2$ and $H_2O$ that desorb in TPRS features that are similar to those observed in the present study for $C_2H_6$ oxidation on $IrO_2$(110). This similarity suggests that common reaction steps control the rates of CO, $CO_2$ and $H_2O$ production during the oxidation of $CH_4$ and $C_2H_6$ on $IrO_2$(110), after initial C—H bond cleavage. We previously reported that $CH_4$ oxidation to CO, $CO_2$ and $H_2O$ is favored at low $CH_4$ coverage, but that recombinative desorption of $CH_4$ competes with oxidation at higher initial $CH_4$ coverage.[10] Our current results demonstrate that $C_2H_6$ also preferentially oxidizes during TPRS when the initial $C_2H_6$ coverage is sufficiently low. A key difference is that $C_2H_6$ dehydrogenates to $C_2H_4$ on $IrO_2$(110) at high initial $C_2H_6$ coverage rather than recombinatively desorbing, and generates $C_2H_4$ at relatively low temperature (~300 to 450 K).

We show below that the coverage of $HO_{br}$ groups plays a decisive role in determining the branching between $C_2H_6$ oxidation and $C_2H_4$ production. The proposed steps for $C_2H_6$ activation and subsequent dehydrogenation on $IrO_2$(110) are the following, Initial $C_2H_6$ dissociation vs. desorption: $C_2H_6(ad)$ 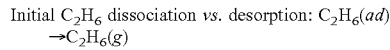
→$C_2H_6(g)$ $C_2H_6(ad)+O_{br}→C_2H_5(ad)+HO_{br}$ 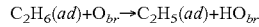

$C_2H_5$ dehydrogenation: $C_2H_5(ad)+O_{br}→C_2H_4(ad)+$ 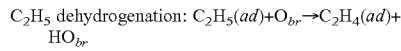
$HO_{br}$ $C_2H_4$ dehydrogenation vs. desorption: $C_2H_4(ad)+$ 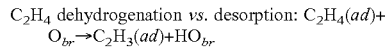
$O_{br}→C_2H_3(ad)+HO_{br}$ $C_2H_4(ad)→C_2H_4(g)$ 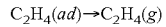

Ethane initially adsorbs in a molecular state $C_2H_6(ad)$ and forms a σ-complex by datively bonding with $Ir_{cus}$ atoms, and a competition between dissociation and desorption of the $C_2H_6(ad)$ species determines the net probability of initial C—H bond cleavage. Our TPRS results show that dissociation of the $C_2H_6(ad)$ species is strongly favored over desorption at low $C_2H_6$ coverages. Since dissociation of the $C_2H_6(ad)$ species requires an $O_{br}$ atom, a decrease in the coverage of $O_{br}$ atoms via conversion to $HO_{br}$ groups may be mainly responsible for $C_2H_6$ dissociation reaching saturation during TPRS beyond a critical $C_2H_6$ coverage. After initial dissociation, the resulting $C_2H5(ad)$ species can dehydrogenate to $C_2H_4(ad)$ species, and the $C_2H_4(ad)$ species can either desorb or further dehydrogenate via H-atom transfer to an $O_{br}$ atom. Again, the coverage of $O_{br}$ atoms decreases with increasing $C_2H_6$ coverage because an increasing fraction of the $O_{br}$ atoms is converted to $HO_{br}$ groups via dehydrogenation of the $C_2H_6$-derived species. According to the proposed reaction steps, $C_2H_4$ desorption should become favored as the $O_{br}$ atom coverage decreases.

Figure 2:
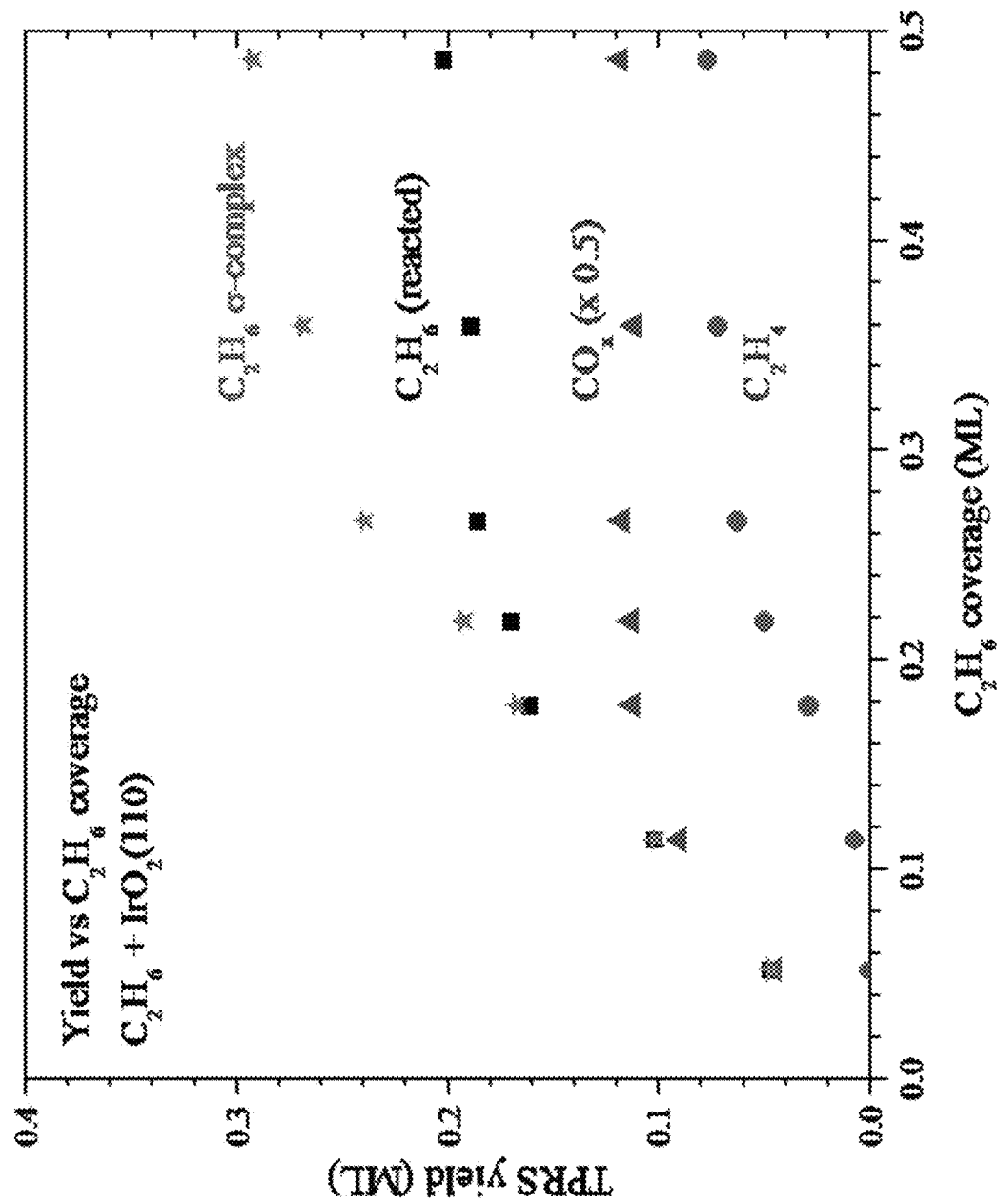
FIG. 2 is an example of TPRS product yields as a function of the initial coverage of $C_2H_6$ adsorbed on $IrO_2(110)$ at 90 K, including the initial coverage of $C_2H_6$ σ-complexes (desorbed+reacted), the reacted yield of $C_2H_6$, the $C_2H_4$ yield and the yield of ethane that oxidizes ($0.5*CO_x$).

Product Yields as a Function of the $C_2H_6$ Coverage FIG. 2 shows the initial and reacted TPRS yields of $C_2H_6$ σ-complexes as a function of the initial $C_2H_6$ coverage on $IrO_2$(110) as well as the yields of $C_2H_6$ that converts to $C_2H_4$ vs. oxidizing to $CO_x$ species. We set the total reacted yield of $C_2H_6$ equal to the sum of the $C_2H_4$ yield plus one half of the yield of $CO+CO_2$, where the factor of one half converts the $CO_x$ yield to the amount of $C_2H_6$ that oxidizes, and we define the initial amount of $C_2H_6$ δ-complexes as equal to the reacted $C_2H_6$ yield plus the amount of $C_2H_6$ that desorbs in the TPRS feature above ~135 K. Our results show that 90 to 100% of the strongly-bound $C_2H_6$ reacts during TPRS as the $C_2H_6$ coverage increases to ~0.25 ML, at which point the yield of reacted $C_2H_6$ begins to plateau toward a value of 0.20 ML and the yield of $C_2H_6$ σ-complexes that desorb concurrently increases. The reacted $C_2H_6$ yield corresponds to about 67% of the adsorbed $C_2H_6$ complexes at saturation. Our results demonstrate that a large quantity of $C_2H_6$ reacts on $IrO_2$(110) during TPRS, and thus support the conclusion that initial C—H activation and subsequent reaction occur on the crystalline terraces of $IrO_2$(110).

Our results further show that $C_2H_6$ oxidation is strongly favored at low coverage, and that $C_2H_4$ production initiates at moderate coverage as the $CO_x$ yield begins to saturate. The yield of oxidized ethane increases nearly to saturation with increasing $C_2H_6$ coverage to about 0.15 ML, and thereafter plateaus at a value of about 0.12 ML. Ethylene production first becomes evident at a $C_2H_6$ coverage above 0.10 ML and increases toward a plateau value as the total $C_2H_6$ coverage rises to ~0.30 ML. The maximum $C_2H_4$ yield is equal to 0.08 ML at saturation of the $C_2H_6$ σ-complexes, and represents a large fraction (~38%) of the $C_2H_6$ that reacts on $IrO_2$(110). The evolution of the product yields with the $C_2H_6$ coverage suggests that the availability of $O_{br}$ atoms plays a decisive role in determining the reaction pathways that adsorbed $C_2H_6$ molecules can access on $IrO_2$(110). Notably, our current results show that the $CO_x$ yield saturates at an $O_{br}$:$C_2H6$ ratio close to five; however, the actual minimum $O_{br}$:$C_2H6$ ratio needed to promote $C_2H_6$ oxidation to $CO_x$ may be less than five because background $H_2$ adsorption converts ~0.15 to 0.25 ML of the initial $O_{br}$ atoms to $HO_{br}$ groups prior to the $C_2H_6$ TPRS experiment.

Enhanced Selectivity for $C_2H_4$ Production on H-Covered $IrO_2$(110)

Figures 3A, 3B:
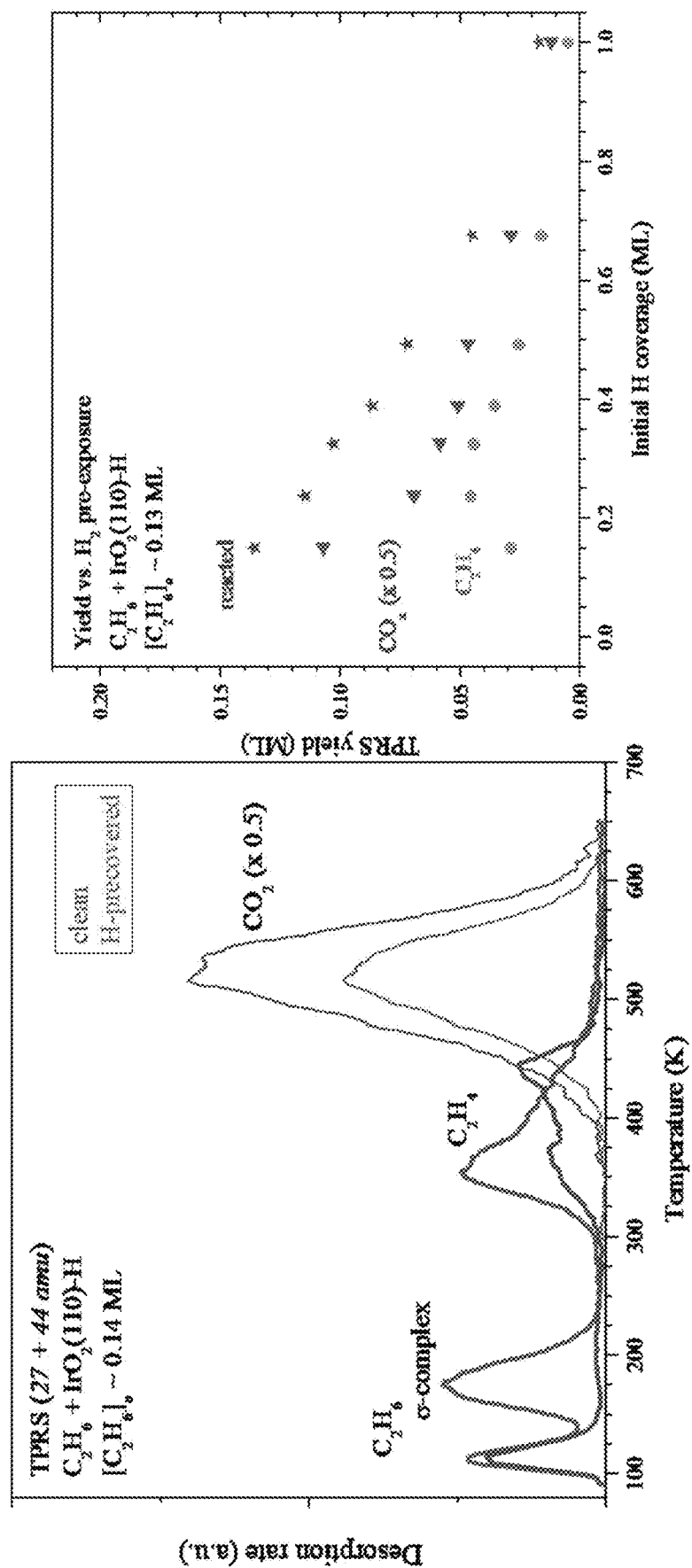
FIG. 3A is an example showing TPRS traces of m/z=27 and 44 obtained after adsorbing ~0.14 ML of $C_2H_6$ at 90 K on a (nominally) clean $IrO_2(110)$ surface (blue) and an $IrO_2(110)$ surface with a hydrogen pre-coverage of 0.32 ML (red). The 27 and 44 amu traces are represented by thick vs. thin lines.
FIG. 3B shows the total reacted $C_2H_6$ yield, oxidized $C_2H_6$ yield ($0.5*CO_x$) and $C_2H_4$ yield obtained as a function of the hydrogen pre-coverage during TPRS for a $C_2H_6$ coverage of ~0.13 ML.

We find that the selectivity toward $C_2H_4$ production from $C_2H_6$ can be enhanced by pre-hydrogenating the $IrO_2$(110) surface. FIG. 3A compares TPRS traces of the 27 and 44 amu fragments obtained after adsorbing ~0.14 ML of $C_2H_6$ on clean $IrO_2$(110) vs. an $IrO_2$(110) surface with an estimated H-atom pre-coverage of 0.32 ML. The 27 amu TPRS trace exhibits well-separated features arising from $C_2H_6$ and $C_2H_4$, and the 44 amu feature alone is sufficient for representing the change in $CO_x$ production because surface hydrogenation causes similar changes in the CO and $CO_2$ TPRS features.

Our results show that pre-hydrogenating the surface to a moderate extent (<~0.4 ML) causes the $CO_2$ TPRS peak to diminish, while the $C_2H_4$ TPRS feature intensifies and skews toward lower temperature, with the maximum shifting from 445 to 350 K. Pre-hydrogenation also causes a $C_2H_6$ TPRS peak at ~175 K to gain intensity, whereas this peak is negligible after generating a moderate $C_2H_6$ coverage on clean $IrO_2$(110) (SI). These changes show that pre-hydrogenating $IrO_2$(110) suppresses $C_2H_6$ oxidation to $CO_x$ species but enhances $C_2H_4$ production when the H-atom pre-coverage is moderate. The concurrent increase in the $C_2H_6$ TPRS peak at 175 K correlates with the decrease in $CO_x$ TPRS yields, and thus demonstrates that surface pre-hydrogenation causes a fraction of the adsorbed $C_2H_6$ σ-complexes to desorb rather than oxidize. This behavior provides further evidence that adsorbed $C_2H_6$ σ-complexes serve as precursors to reaction and that dissociation involves H-atom transfer to $O_{br}$ atoms.

FIG. 3B shows how the total TPRS yield of reacted $C_2H_6$ as well as the yields of the $C_2H_4$ and $CO_x$ reaction products evolve as a function of the initial H-atom coverage on $IrO_2$(110), for an initial $C_2H_6$ coverage of 0.13±0.015 ML. We estimate that the nominally clean $IrO_2$(110) surface was covered by ~0.15 ML of H-atoms prior to ethane adsorption. Our results show that the total yield of reacted $C_2H_6$ decreases monotonically with increasing H-atom pre-coverage, indicating that initially converting $O_{br}$ atoms to $HO_{br}$ groups suppresses $C_2H_6$ activation on $IrO_2$(110). The $CO_x$ yield decreases sharply and continuously from a value of 0.11 to 0.01 ML as the H-atom coverage increases to about 1 ML. In contrast, however, the $C_2H_4$ yield increases from ~0.03 to 0.045 ML with increasing H-atom coverage to ~0.32 ML, and thereafter decreases, reaching a final value of 0.005 ML at saturation of the initial H-atom layer. These changes represent a nearly threefold increase in the selectivity for $C_2H_4$ production, as measured by the ratio of ethane that converts to ethylene vs $CO_x$ species. The $C_2H_4$ yield begins to fall below its value on the (nominally) clean $IrO_2(110)$ surface when the initial H-atom coverage starts to exceed 0.5 ML. The evolution of product yields with increasing H-coverage demonstrates that $O_{br}$ atoms are needed to promote the initial C—H activation of $C_2H_6$ on $IrO_2(110)$ as well as further dehydrogenation and that the controlled deactivation of $O_{br}$ atoms by hydrogenation provides a means to enhance reaction selectivity to favor the conversion of ethane to ethylene.

Pathways for $C_2H_6$ Dehydrogenation on $IrO_2(110)$

We examined several possible $C_2H_6$ adsorption configurations (FIGS. 8A-8D) and predict that $C_2H_6$ forms a strongly-bound σ-complex on $IrO_2(110)$ by adopting a flat-lying geometry along the $Ir_{cus}$ row in which each $CH_3$ group forms a H—$Ir_{cus}$ dative bond (a $2\eta^1$ configuration) and the $C_2H_6$ molecule effectively occupies two $Ir_{cus}$ sites. This staggered $2\eta^1$ configuration is similar to that predicted by Pham et al. but they report an eclipsed $C_2H_6$ $2\eta^1$ configuration,[22] which we find to be less stable than the staggered configuration by ~9 kJ/mol (FIGS. 8A-8D). We have previously reported that $C_2H_6$ complexes on $PdO(101)$ and $RuO_2(110)$ also preferentially adopt the $2\eta^1$ configuration.[18,23-24]

Figure 4A:
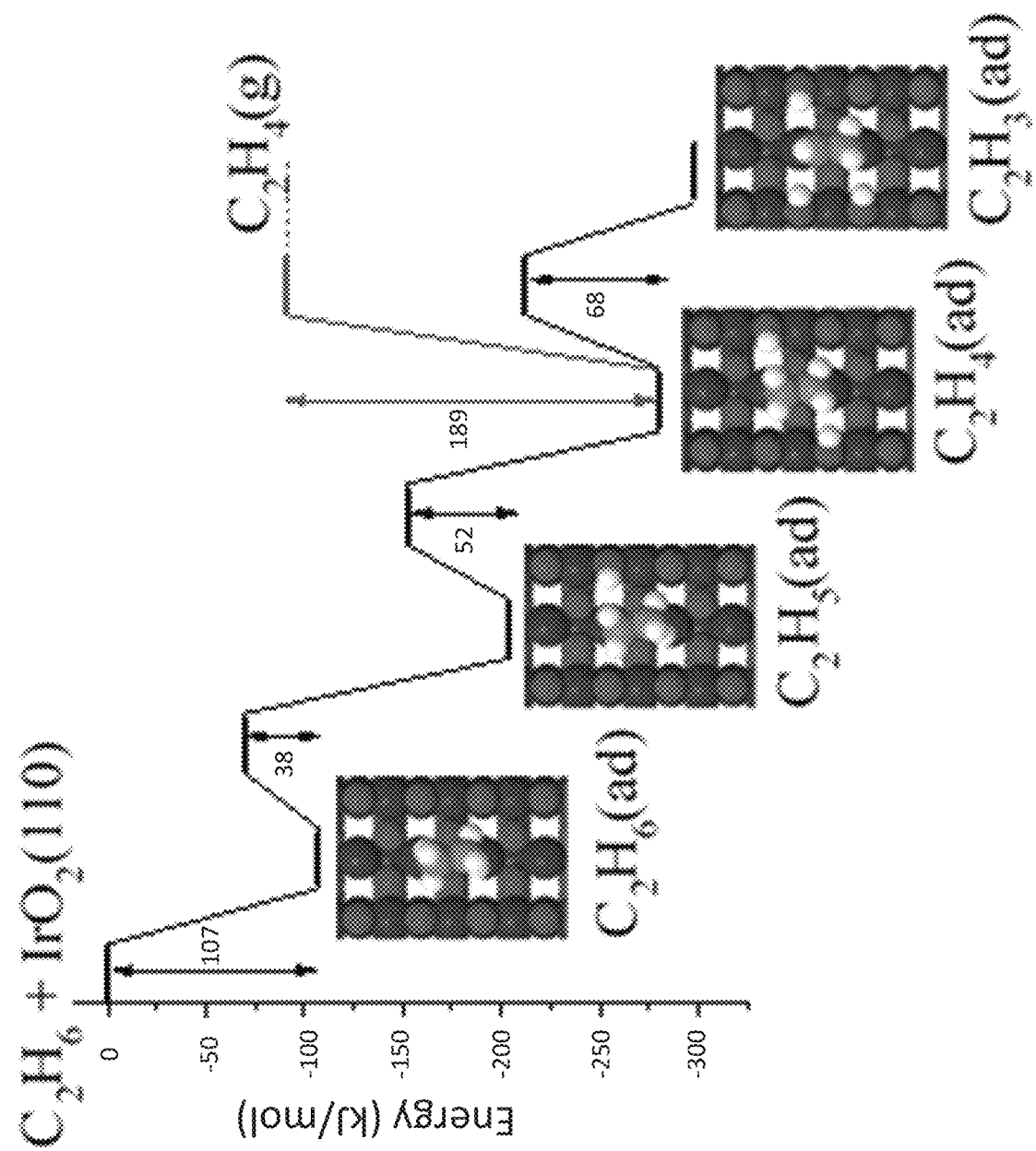
FIGS. 4A-4B show examples of energy pathways for the dehydrogenation of $C_2H_6$ adsorbed on $IrO_2(110)$ as computed using DFT-D3 for surfaces initially containing (FIG. 4A) zero and (FIG. 4B) two $HO_{br}$ groups. The final reaction step compares the energy changes for $C_2H_4$ desorption (red) vs. dehydrogenation to a $C_2H_3$(ad) species (black). A comparison of the energetics for these pathways with and without D3 can be found in Table 1.

FIG. 4A shows the energy diagram computed using DFT-D3 for the sequential dehydrogenation of $C_2H_6$ to $C_2H_4$ on $IrO_2(110)$, followed by either $C_2H_4$ desorption (red) or $C_2H_4$ dehydrogenation to adsorbed $C_2H_3$. DFT-D3 predicts that the $2\eta^1$ $C_2H_6$ complex achieves a binding energy of 107 kJ/mol on clean $IrO_2(110)$ and that the barrier for C—H bond cleavage via H-transfer to an $O_{br}$ atom is only 38 kJ/mol. According to the calculations $C_2H_6$ dehydrogenation to produce $C_2H_5$—$Ir_{cus}$ and $HO_{br}$ species is exothermic by about 97 kJ/mol, and the barrier for reaction is significantly lower than the binding energy of the adsorbed $C_2H_6$ complex (38 vs. 107 kJ/mol). We find that DFT-PBE calculations without dispersion corrections underestimate the $C_2H_6$ binding energy on $IrO_2(110)$, but still predict that the $C_2H_6$ dissociation barrier is lower than the desorption barrier (Table 1). Our calculations thus predict that $C_2H_6$ C—H bond cleavage is strongly favored over molecular desorption on clean $IrO_2(110)$ such that all adsorbed $C_2H_6$ molecules will dissociate at low temperature, provided that $O_{br}$ atoms are available for reaction. This prediction agrees well with our experimental finding that $C_2H_6$ dissociates on $IrO_2(110)$ with near unit probability at low $C_2H_6$ coverages (FIG. 2).

We find that the adsorbed $C_2H_5$ group on $IrO_2(110)$ can also dehydrogenate by a low energy pathway wherein the $CH_3$ group transfers a H-atom to an $O_{br}$ atom, resulting in an adsorbed $C_2H_4$ species and a $HO_{br}$ group located in the opposing row from the initial $HO_{br}$ group (FIG. 4A). DFT-D3 predicts an energy barrier of 52 kJ/mol for this reaction and an exothermicity of 75 kJ/mol. The barrier for $C_2H_5$ dehydrogenation is relatively low because the $CH_3$ group maintains a H—$Ir_{cus}$ dative interaction that weakens one of the C—H bonds. The $C_2H_4$ product adopts a bidentate geometry in which a C—$Ir_{cus}$ σ-bond forms at each $CH_2$ group (i.e., di-σ configuration). Our calculations predict that the $C_2H_4$ species needs to overcome a barrier of 189 kJ/mol to desorb vs. a barrier of 68 kJ/mol to dehydrogenate via H-transfer to an $O_{br}$ atom, affording an adsorbed $C_2H_3$ species and a third $HO_{br}$ group. The calculations thus predict that $C_2H_4$ dehydrogenation is strongly favored over $C_2H_4$ desorption when $O_{br}$ atoms are available to serve as H-atom acceptors. This prediction is consistent with our experimental observation that $C_2H_6$ oxidation occurs preferentially over $C_2H_4$ production at low initial $C_2H_6$ and $HO_{br}$ coverages.

Figure 4B:
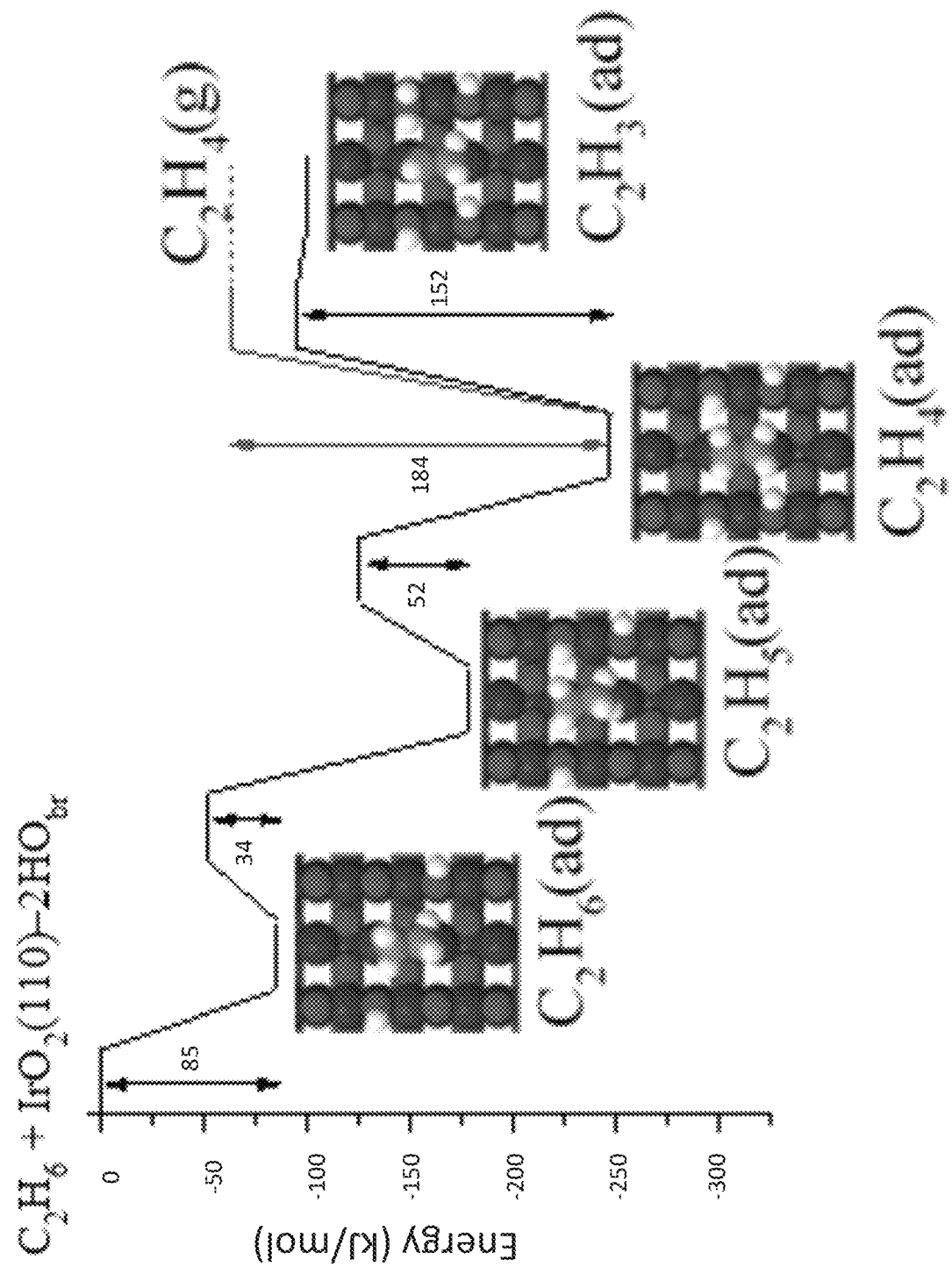

FIG. 4B shows the computed pathway for $C_2H_6$ dehydrogenation on $IrO_2(110)$ when two of the four accessible $O_{br}$ atoms are initially hydrogenated to $HO_{br}$ groups. For these calculations, we hydrogenated $O_{br}$ atoms located in opposing rows, with each next to a different $CH_3$ group of the $C_2H_6$ complex (FIG. 4B). Our calculations predict that hydrogenation of the two $O_{br}$ atoms destabilizes the $C_2H_6$ σ-complex on $IrO_2(110)$ by about 22 kJ/mol. We have recently reported that the hydrogenation of $O_{br}$ atoms also destabilizes $H_2$ complexes on $IrO_2(110)$.[11] Our calculations also predict that the energy barriers are nearly the same for $C_2H_6$ and $C_2H_5$ dehydrogenation on the initially clean $IrO_2(110)$ vs. pre-hydrogenated $IrO_2(110)$-$2HO_{br}$ surfaces when reaction occurs by H-transfer to an $O_{br}$ atom (FIGS. 4A, 4B).

Sequential dehydrogenation of $C_2H_6$ to $C_2H_4$ on the initial $IrO_2(110)$-$2HO_{br}$ surface converts all four of the accessible $O_{br}$ atoms to $HO_{br}$ groups, and causes $C_2H_4$ desorption to become favored over further dehydrogenation because $HO_{br}$ groups are much less reactive than $O_{br}$ atoms. The energy barrier for $C_2H_4$ dehydrogenation via H-transfer to a $HO_{br}$ group is 152 kJ/mol, compared with 68 kJ/mol for $C_2H_4$ dehydrogenation to an $O_{br}$ atom. In addition, the reverse reaction features an energy barrier of only 5 kJ/mol so the $H_2O_{br}$ species would rapidly transfer a H-atom to $C_2H_3$ to regenerate the adsorbed $C_2H_4$ and $HO_{br}$ species. Our DFT calculations thus indicate that $C_2H_4$ desorption is favored over dehydrogenation when all of the accessible $O_{br}$ atoms are hydrogenated to $HO_{br}$. This prediction agrees well with our experimental findings that pre-hydrogenation of $IrO_2$(110) promotes the conversion of $C_2H_6$ to $C_2H_4$ while suppressing $C_2H_6$ oxidation, and that $C_2H_4$ production begins to occur on initially clean $IrO_2(110)$ only at moderate initial $C_2H_6$ coverages.

Structure of the s-$IrO_2(110)$ Layer on $Ir(100)$

Figure 5:
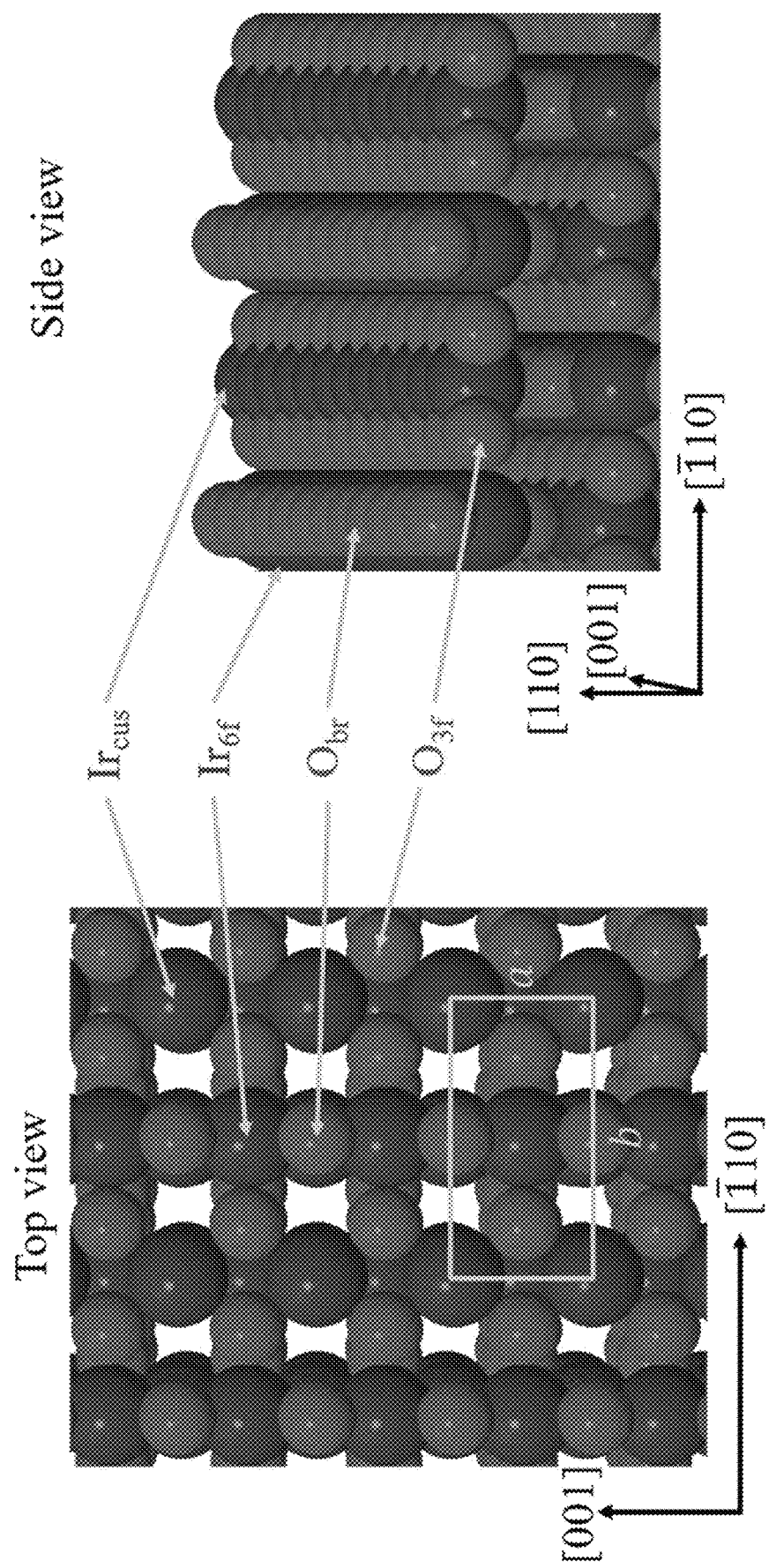
FIG. 5 is a model representation of top and side view of stoichiometric $IrO_2(110)$ structure. The red and blue atoms represent O and Ir atoms, respectively. Rows of $Ir_{cus}$, $Ir_{6f}$, $O_{br}$, $O_{3f}$ along the [001] crystallographic direction are indicated. The unit cell dimensions a and b are parallel to the [001] and [$\bar{1}$10] directions of the $IrO_2$ crystal.
Figure 6A:
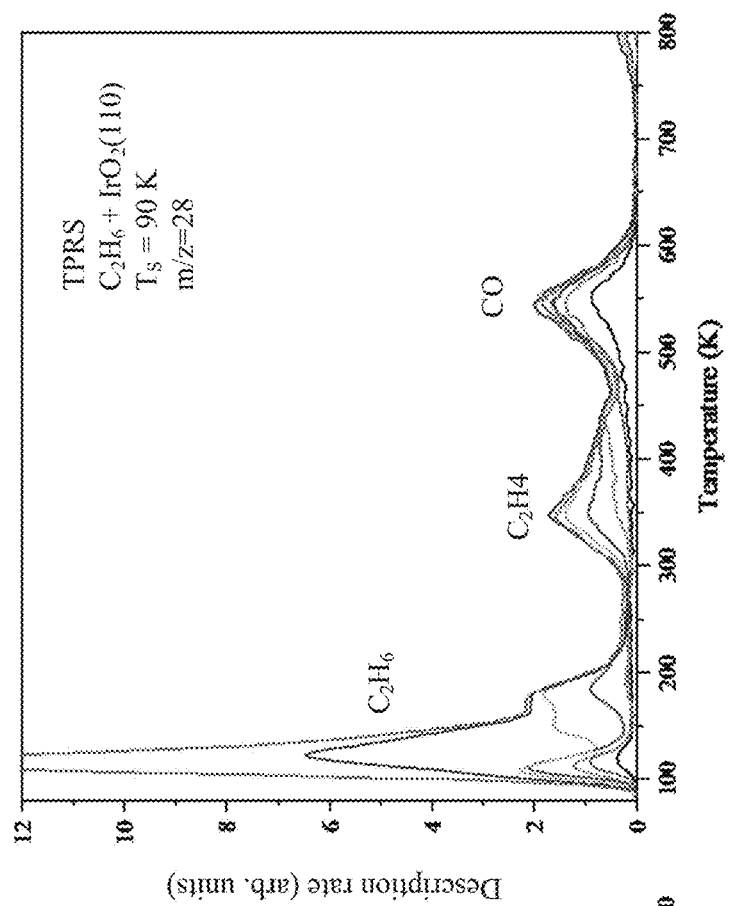
FIGS. 6A-6D TPRS are examples of spectra obtained after adsorbing $C_2H_6$ on $IrO_2(110)$ at 90 K to generate coverages of 0.05, 0.11, 0.18, 0.22, 0.27, 0.36 and 0.49 ML. TPRS traces are shown for (FIG. 6A) m/z=27, (FIG. 6B) m/z=28, (FIG. 6C) m/z=29 and (FIG. 6D) m/z=44 and the features arising from specific compounds are labeled.
Figure 6B:
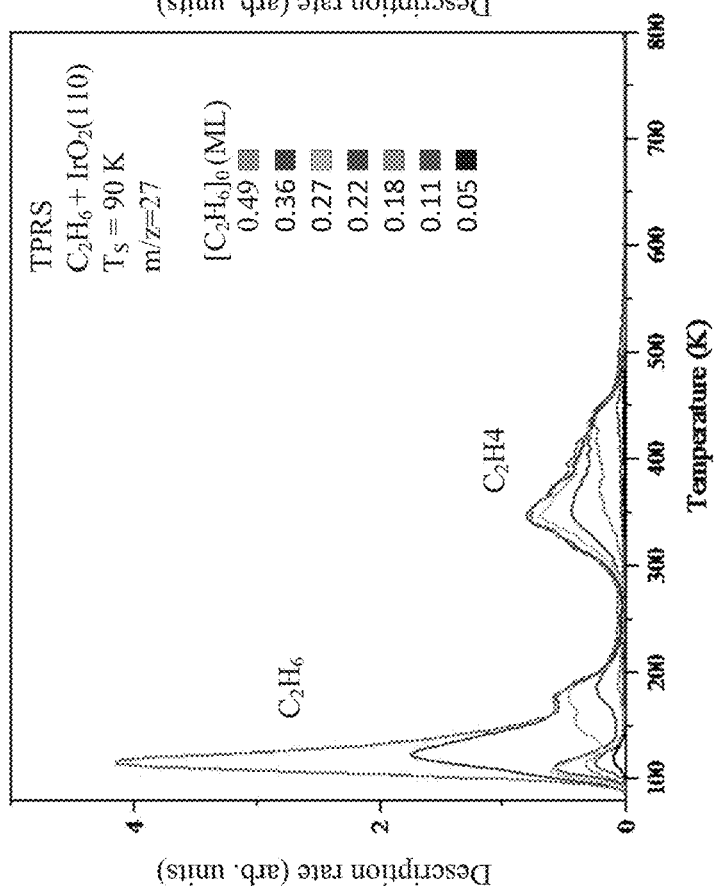
Figure 6D:
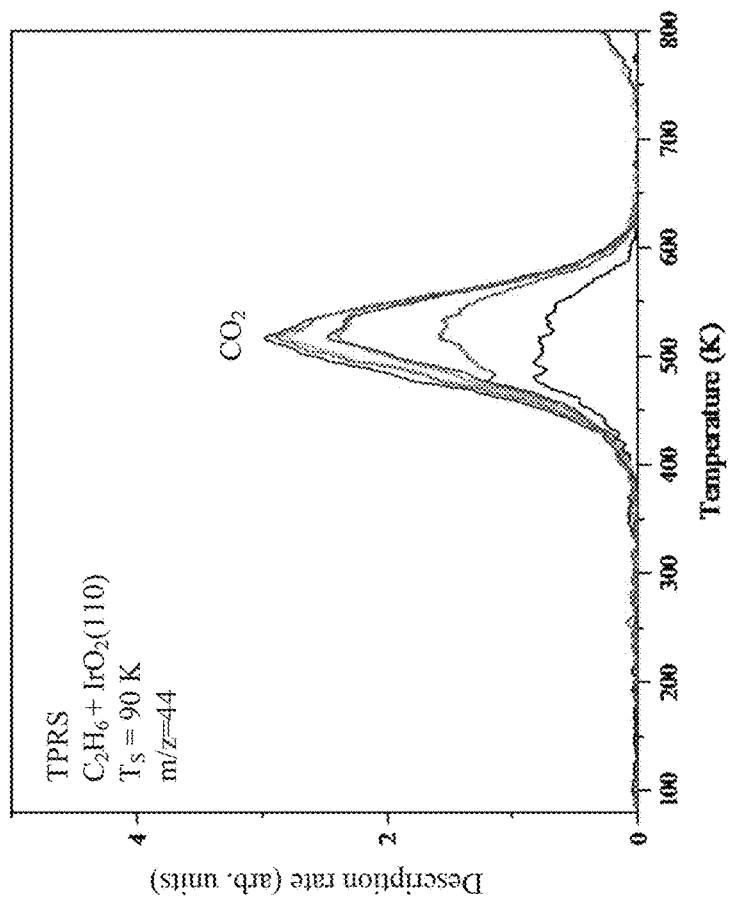
Figure 6C:
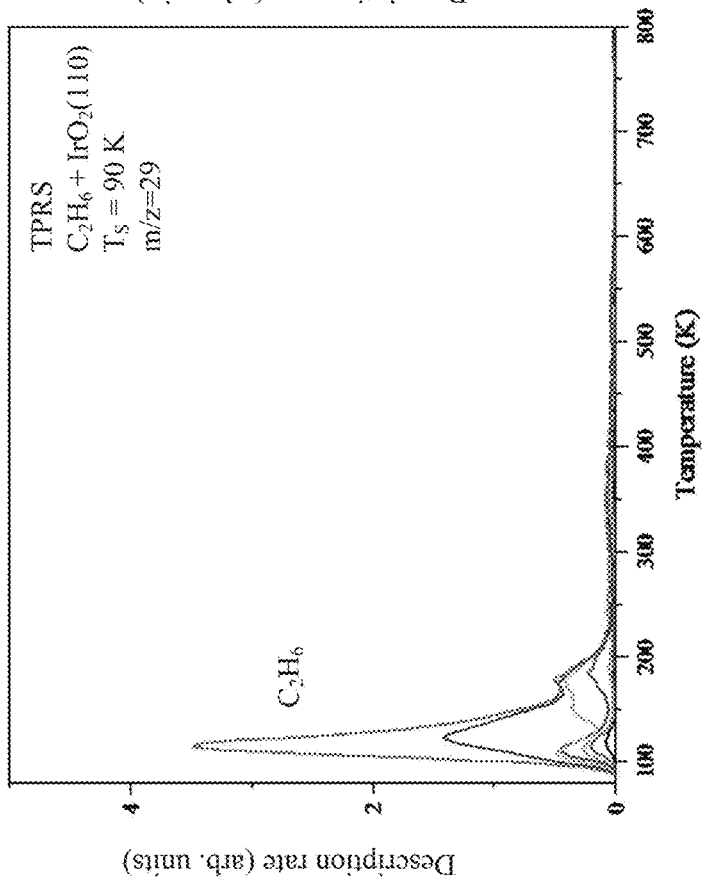

Bulk crystalline $IrO_2$ has a tetragonal unit cell with Ir atoms surrounded by an octahedral arrangement of six oxygen atoms and each oxygen atom is coordinated with three Ir atoms resulting in a trigonal plane. FIG. 5 shows a top and side view of the stoichiometrically-terminated $IrO_2$(110) surface. The $IrO_2(110)$ surface unit cell is rectangular with dimensions of a=3.16 Å and b=6.36 Å, where a and b are parallel to the [001] and [1̄10] directions of the $IrO_2$ crystal, respectively. The unit cell dimensions may also be expressed as a a=1.16x and b=2.34x, where x=2.72 Å is the lattice constant of Ir(100). The $IrO_2(110)$ surface consists of alternating rows of $O_{br}$ and $Ir_{cus}$ that align along the [001] direction. Each of these surface species has one dangling bond due to a decrease in coordination in comparison to bulk $IrO_2$.

Measurement of Product Yields

We estimate atomic oxygen coverages by scaling integrated $O_2$ TPD spectra with those obtained from a saturated (2×1)—O layer containing 0.50 ML of O-atoms and prepared by exposing the Ir(100)-(5×1) surface to $O_2$ in UHV.[27] To estimate hydrogen coverages, we scaled integrated hydrogen desorption spectra by an integrated TPD spectrum collected from a saturated Ir(100)-(5×1)-H layer containing 0.80 ML of atomic hydrogen that we prepared by adsorbing hydrogen to saturation on the Ir(100)-(5×1) surface at 300 K.[28] We performed TPRS experiments of CO oxidation on saturated 0-covered Ir(100) to estimate the $CO_2$ desorption yields. Specifically, we collected $O_2$ and $CO_2$ TPRS spectra after exposing a (2×1)—O layer to a sub-saturation dose of CO and assuming that the $CO_2$ yield is equal to the difference between the initial (0.50 ML) and final coverages of oxygen as determined from the $O_2$ TPRS yield. To estimate CO desorption yields, we scaled integrated CO desorption spectra by an integrated TPD spectrum collected from a saturated c(2×2) layer containing 0.50 ML of CO that we prepare by adsorbing CO to saturation on Ir(100)-(1×1) at 300 K.[27,29,30]

We performed TPRS experiments of hydrogen oxidation on partially O-covered Ir(100) to estimate the water desorption yields. In these experiments, we first collected $O_2$ and $CO_2$ TPRS spectra after exposing a (2×1)—O layer to a sub-saturation dose of CO and assuming that the oxygen remaining on Ir(100) is equal to the difference between the initial oxygen coverage in the (2×1)—O layer (0.50 ML) and the $CO_2$ yield determined from the $CO_2$ TPRS spectrum. We then collected $O_2$ and $H_2O$ TPRS spectra after exposing the partially 0-covered Ir(100) surface generated from the first step to a saturation dose of hydrogen and assuming that the water yield is equal to the difference between the initial and finial coverage of oxygen determined from the $O_2$ TPRS yield. We repeat these calibration TPRS experiments to ensure accuracy in our estimates of desorption yields. We estimate $C_2H_6$ and $C_2H_4$ coverages by scaling the intensity-to-coverage conversion factors determined for CO with relative sensitivity factors reported for the mass spectrometric detection of these gases.

TPRS Spectra as a Function of the $C_2H_6$ Coverage on $IrO_2(110)$

FIGS. 6A-6D show TPRS spectra of mass fragments m/z=27, 28, 29 and 44 obtained as a function of the initial $C_2H_6$ coverage generated on $IrO_2(110)$ at 90 K. The mass-fragment TPRS spectra clearly illustrate the TPRS features that arise from $C_2H_6$, $C_2H_4$ and CO because these species desorb in well-separated temperature ranges. We deconvoluted selected mass-fragment TPRS spectra to generate the TPRS spectra for $C_2H_6$, $C_2H_4$ and CO that we report in FIG. 1. This deconvolution involves first subtracting the m/z=29 spectrum from the m/z=27 spectrum after rescaling the m/z=29 spectrum so that the intensities of the TPRS peaks below 250 K are equal in the m/z=29 and 27 spectra. This step removes the $C_2H_6$ contribution from the m/z=27 spectrum and generates a TPRS spectrum for only $C_2H_4$. We obtain a CO TPRS spectrum by first subtracting the $C_2H_6$ contribution from the m/z=28 spectrum, and then subtracting the $C_2H_4$ contribution as obtained from the corrected m/z=27 spectrum.

As discussed in the example above, the TPRS spectra demonstrate that CO and $CO_2$ production dominates at low $C_2H_6$ coverage and that the corresponding CO and $CO_2$ TPRS peaks are nearly saturated once the initial $C_2H_6$ coverage increases to ~0.15 ML. Ethylene desorption becomes evident at an initial $C_2H_6$ coverage of ~0.1 ML and the $C_2H_4$ TPRS feature intensifies with increasing coverage thereafter until saturating at an initial $C_2H_6$ coverage of ~0.30 ML. We attribute the $C_2H_6$ TPRS feature at 150-185 K to strongly-bound $C_2H_6$ σ-complexes and estimate that this feature saturates when the total $C_2H_6$ coverage reaches 0.30 ML. The $C_2H_6$ TPRS peak at ~110 K intensifies slowly as the initial $C_2H_6$ coverage increases to ~0.30 ML and saturates at a yield of only about 0.025 ML, consistent with a minority species. A separate $C_2H_6$ TPRS peak at ~120 K intensifies sharply with increasing $C_2H_6$ coverage above 0.30 ML, and is consistent with $C_2H_6$ adsorbed on $O_b$ sites of $IrO_2(110)$ based on similar behavior observed during $C_2H_6$ adsorption on $RuO_2(110)$ and $TiO_2(110)$.[31,20]

TPRS spectra from $C_2H_4$ on $IrO_2(110)$

Figure 7B:
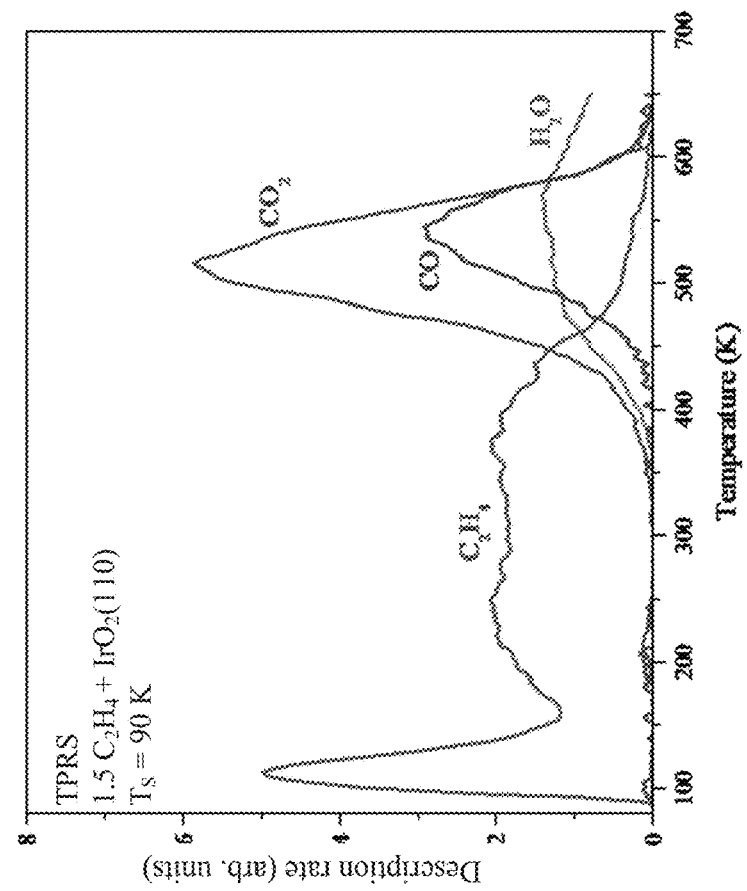
FIGS. 7A-7B are examples of TPRS spectra obtained after exposing $IrO_2(110)$ to a) 0.8 L and b) 1.5 L of $C_2H_4$ at 90 K.
Figure 7A:
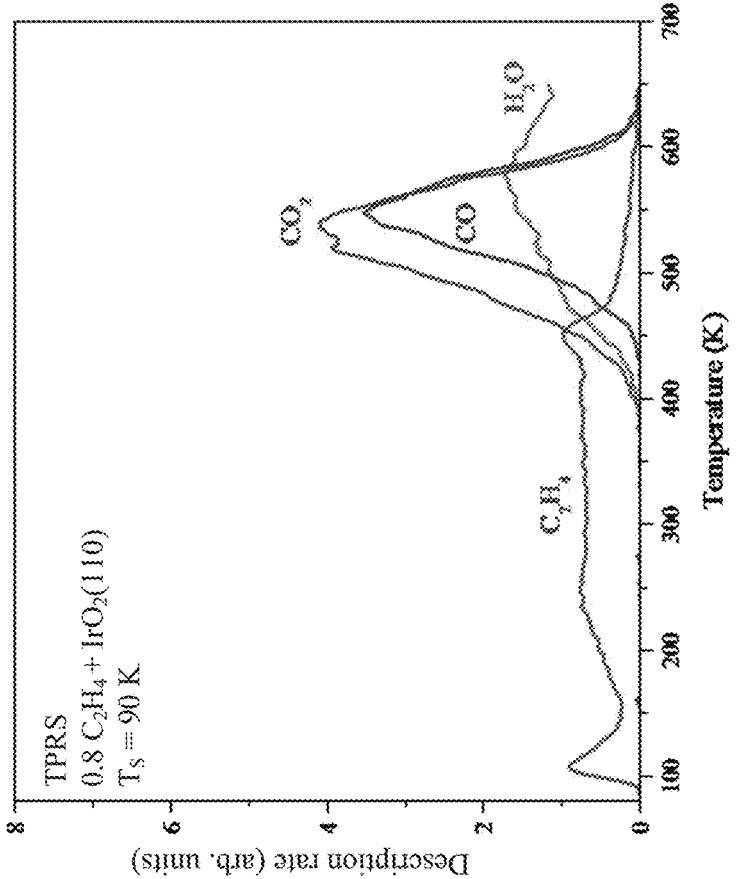

FIGS. 7A and 7B show TPRS spectra obtained after exposing $IrO_2(110)$ to 0.8 and 1.5 L of $C_2H_4$ at 90 K, where the 1.5 L exposure causes saturation of the desorption features above 150 K. A fraction of the adsorbed $C_2H_4$ oxidizes and produces CO, $CO_2$ and $H_2O$ that desorb in TPRS features above 400 K, where these features are nearly identical to those observed during our TPRS experiments with $C_2H_6$ as described in the present disclosure. The sharp $C_2H_4$ TPRS peak at 111 K arises from weakly-bound $C_2H_4$ molecules that are likely associated with the $O_b$ atoms of $IrO_2(110)$ or a minority surface phase. We attribute the broad $C_2H_4$ TPRS feature between ~150 and 500 K to $C_2H_4$ adsorbed strongly on the $Ir_{cus}$ atoms. At the lower coverage, a distinct $C_2H_4$ TPRS peak is evident at 450 K. This feature appears as a shoulder at higher coverage and the $C_2H_4$ desorption rate remains nearly constant between 200 and 400 K. Ethylene adsorption on $RuO_2(110)$ also produces a broad $C_2H_4$ TPRS feature.[32] We suggest that the significant breadth of the $C_2H_4$ TPRS feature reflects a sensitivity of the $C_2H_4$ binding energy to the local environment, including the coverage of $C_2H_4$ molecules, $HO_{br}$ groups and $C_2H_4$-derived species that serve as intermediates to $CO_x$ formation.

Configurations of $C_2H_6$ Adsorbed on $IrO_2(110)$ as Predicted with DFT

Figure 8A:
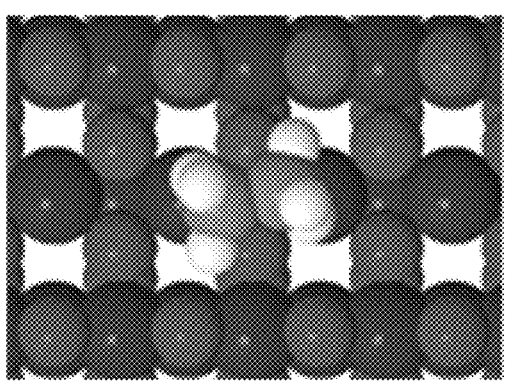
FIGS. 8A-8D are models of the top and side view of ethane adsorbed on $IrO_2(110)$ in (FIG. 8A) $2\eta^1$ (staggered) (FIG. 8B) $2\eta^1$ (eclipsed) (FIG. 8C) $\eta^2$ bridge and (FIG. 8D) $\eta^1$ top with a PBE (PBE-D3) binding energies of 53.7 (107.3), 44.3 (98.9), 14.4 (46.9), 39.9 (79.5) kJ/mol, respectively. The $2\eta^1$ configurations shown in FIGS. 8A and 8B have no imaginary frequencies and thus correspond to minima in the potential energy surface, whereas the configurations shown in 8C and 8D each have one imaginary frequency, indicating that these structures occur at saddle points on the potential energy surface.
Figure 8A:
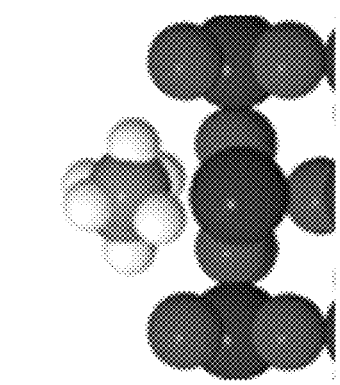
Figure 8B:
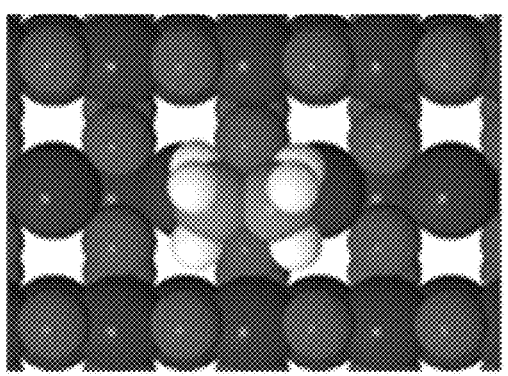
Figure 8B:
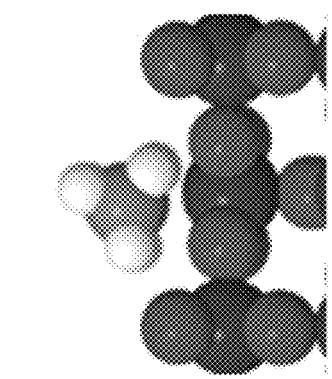
Figure 8C:
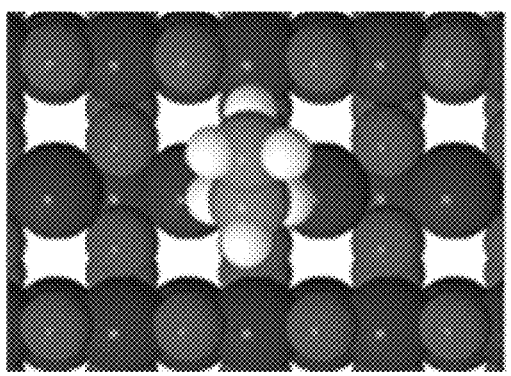
Figure 8C:
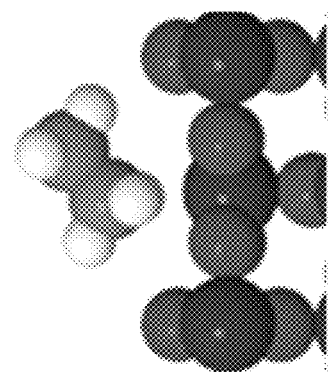
Figure 8D:
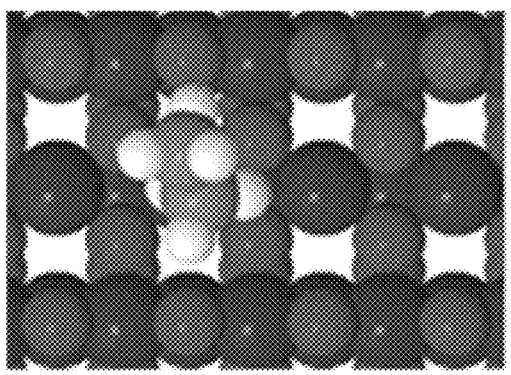
Figure 8D:
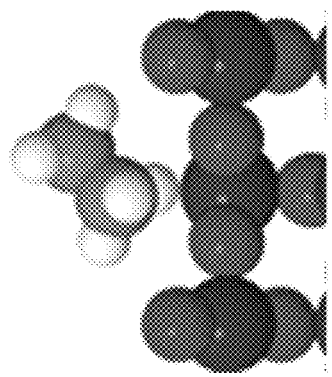

FIGS. 8A-8D show the four configurations for ethane adsorbed on $IrO_2(110)$ that we identified with DFT. Pham and co-workers report that the eclipsed configuration shown in FIG. 8B is the most stable configuration of $C_2H_6$ on $IrO_2(110)$,[22] but we find that the staggered ethane configuration with interactions of the two $CH_3$ groups with $O_{br}$ atoms in opposite rows is more favorable by 9.3 (8.4) kJ/mol with PBE (PBE-D3).

Comparison of DFT-PBE Results with and without Dispersion-Corrections

| Structure | DFT-D3 (PBE) E (kJ/mol) | DFT-D3 (PBE) $E_f$ (kJ/mol) | DFT (PBE) E (kJ/mol) | DFT (PBE) $E_f$ (kJ/mol) | DFT-D3-DFT ΔE (kJ/mol) |
|---|---|---|---|---|---|
| $C_2H_6 + 4O_{br}$ | −107.3 | | −53.7 | | −53.6 |
| $(C_2H_6 + 4O_{br})*$ | −69.4 | 37.9 | −10.5 | 43.2 | −58.9 |
| $C_2H_5 + 3O_{br}/HO_{br}$ | −204.5 | | −149.4 | | −55.1 |
| $(C_2H_5 + 3O_{br}/HO_{br})*$ | −152.2 | 52.3 | −93.9 | 55.5 | −58.3 |
| $C_2H_4 + 2O_{br}/2HO_{br}$ | −279.6 | | −224.1 | | −55.5 |
| $(C_2H_4(g) + 2O_{br}/2HO_{br})*$ | −90.9 | 188.7 | −81.6 | 142.5 | −9.3 |
| $(C_2H_4 + 2O_{br}/2HO_{br})*$ | −211.7 | 67.9 | −152.8 | 71.3 | −58.9 |
| $C_2H_3 + O_{br}/3HO_{br}$ | −298.3 | | −238.7 | | −59.6 |

Table 1 shows energies and energy barriers computed for the adsorption and sequential dehydrogenation of $C_2H_6$ on $IrO_2(110)$ using DFT-PBE with (DFT-D3) and without (DFT) dispersion corrections. The energies determined using DFT-D3 are greater than those computed using DFT by a similar amount of 57.1±2.3 kJ/mol for each structure that includes an adsorbed hydrocarbon species derived from $C_2H_6$. The DFT-D3 calculations using the PBE functional overestimate the binding energies of $C_2H_6$ and $C_2H_4$ on $IrO_2(110)$ determined from our TPRS data, to an extent that is similar to our previous results for $CH_4$ and $H_2$ adsorbed on $IrO_2(110)$.[10, 11] Calculations using other dispersion-corrected functionals also overestimate the binding energy of $C_2H_6$ on $IrO_2(110)$.[22] From TPD, we estimate a binding energy of about 65 kJ/mol for the $C_2H_6$ σ-complex on $IrO_2(110)$, whereas DFT-D3 predicts a value of 107 kJ/mol for $C_2H_6$ adsorbed on clean $IrO_2(110)$. Similarly, the $C_2H_4$ TPRS feature from 300 to 450 K suggests a $C_2H_4$ binding energy on $IrO_2(110)$ between about 130 and 165 kJ/mol, while DFT-D3 predicts of a binding energy of 189 kJ/mol. Our DFT calculations without dispersion slightly underestimate the $C_2H_6$ binding energy on $IrO_2(110)$ (54 vs. 65 kJ/mol), and the computed $C_2H_4$ binding energy falls within the wide range estimated experimentally. Notably, our DFT-PBE calculations without dispersion predict facile $C_2H_6$ C—H bond cleavage on $IrO_2(110)$ and support the conclusion that $C_2H_6$ conversion to $C_2H_4$ is favored over oxidation on partially-hydrogenated $IrO_2(110)$. Although our DFT calculations support the main conclusions of this study, the overbinding predicted by current dispersion-corrected DFT methods signals a need for further development of exchange-correlation functionals that can accurately predict molecular binding on $IrO_2(110)$.

Discussion

Our results show that $C_2H_6$ activation is highly facile on $IrO_2(110)$ at temperatures below 200 K, and that further dehydrogenation produces $C_2H_4$ that desorbs between 300 and 450 K. Based on comparison with reference TPRS data (SI), we conclude that $C_2H_4$ desorption is the rate-limiting step in the conversion of $C_2H_6$ to $C_2H_4$ on $IrO_2(110)$ during TPRS. Our DFT calculations support these conclusions as they predict that the barrier for $C_2H_6$ C—H bond cleavage on clean $IrO_2(110)$ is lower than that for $C_2H_4$ desorption by at least 100 kJ/mol. Indeed, we find that the $IrO_2(110)$ surface is exceptionally active in promoting alkane C—H bond cleavage—we estimate a barrier between 35 and 40 kJ/mol for ethane activation on $IrO_2(110)$, and our prior work reveals an even lower barrier of 28 kJ/mol for $CH_4$ activation on $IrO_2(110)$.[10] In fact, our DFT results predict that initial C—H bond cleavage has the lowest barrier among the reaction steps involved in $C_2H_6$ conversion to $C_2H_4$ on $IrO_2(110)$.

In contrast to $IrO_2(110)$, initial C—H bond activation is the rate-determining step in the ODH of alkanes on most other oxides. Supported vanadium-oxide based catalysts have been widely studied due to their favorable performance in promoting the ODH of ethane and propane.[1, 9] While the specific values can depend on multiple factors, barriers for ethane C—H bond cleavage on $VO_x$-based catalysts lie in a range from about 120 to 150 kJ/mol,[5, 25-26] and reactors are operated at temperatures between 700 and 900 K to achieve optimal rates and selectivity of alkene production from ethane and propane.[2] According to DFT, ethylene desorption is the rate-determining step for the conversion of $C_2H_6$ to $C_2H_4$ on $IrO_2(110)$ under TPRS conditions because the dehydrogenation of adsorbed $C_2H_6$ and $C_2H_5$ groups are both facile processes on clean $IrO_2(110)$ and the $C_2H_4$ product binds strongly. From our TPRS data, we estimate that the barrier for $C_2H_4$ desorption from $IrO_2(110)$ lies between about 130 and 165 kJ/mol, and is thus close to the values reported for $C_2H_6$ C—H activation barriers on $VO_x$-based catalysts. However, since the entropy of activation is much larger for $C_2H_4$ desorption compared with ethane activation, $C_2H_4$ desorbs from $IrO_2(110)$ at lower temperature relative to the temperatures at which $VO_x$-based catalysts would achieve comparable rates of ethane conversion to ethylene.

Our TPRS results show that the desorption of ethylene from $IrO_2(110)$ occurs at lower temperature during TPRS than the reaction-limited desorption of $H_2O$ and $CO_x$ species resulting from ethane oxidation (FIGS. 1A-1B). A possible implication is that low temperature operation can enable $IrO_2$ catalysts to promote the conversion of ethane to ethylene at high rates while minimizing $CO_x$ production. However, the higher desorption temperature of $H_2O$ compared with $C_2H_4$ suggests that $H_2O$ desorption could be a rate-controlling step in the $IrO_2$-promoted conversion of $C_2H_6$ to $C_2H_4$ under steady-state conditions. While further study is needed, our results suggest possibilities for achieving efficient and selective conversion of ethane to ethylene at low temperature using $IrO_2$-based catalysts.

Our results also demonstrate that partial hydrogenation of the $IrO_2(110)$ surface enhances ethane conversion to ethylene while suppressing extensive oxidation to $CO_x$ species. We find that $HO_{br}$ groups are significantly less active than $O_{br}$ atoms as H-atom acceptors, and, as a result, hydrogenating a fraction of the $O_{br}$ atoms limits the extent to which adsorbed hydrocarbons can dehydrogenate and causes $C_2H_4$ desorption to become favored over further dehydrogenation and extensive oxidation. This behavior provides a viable explanation of the evolution of TPRS product yields with increasing $C_2H_6$ coverage. At low $C_2H_6$ coverage enough $O_{br}$ atoms are available to allow each $C_2H_6$ molecule to extensively dehydrogenate, and produce intermediates that oxidize to $CO_x$ species with further heating. With increasing $C_2H_6$ coverage, the extent to which $C_2H_6$ molecules dehydrogenate becomes limited because a larger fraction of $O_{br}$ atoms convert to $HO_{br}$ groups and deactivate. Consistent with this interpretation, our experiments demonstrate that the selectivity toward ethane conversion to ethylene can be enhanced by partially hydrogenating the $IrO_2(110)$ surface prior to adsorbing ethane. This finding may have broad implications for developing methods by which to modify the selectivity of $IrO_2$ catalysts. In particular, our results demonstrate that controllably deactivating a fraction of the reactive O-atoms of $IrO_2$ is an effective approach for promoting the partial dehydrogenation of ethane over extensive oxidation.

Summary

We investigated the dehydrogenation of ethane on the stoichiometric $IrO_2(110)$ surface using TPRS and DFT calculations. Our results show that ethane forms strongly-bound σ-complexes on $IrO_2(110)$ and that a large fraction of the adsorbed complexes undergo C—H bond cleavage below 200 K during TPRS. Our DFT calculations predict that ethane σ-complexes on $IrO_2(110)$ dissociate by a heterolytic mechanism involving H-atom transfer to a neighboring $O_{br}$ atom, and that the barrier for C—H bond cleavage is lower than the binding energy of the $C_2H_6$ σ-complex. We find that the resulting ethyl groups react with the $IrO_2(110)$ surface via oxidation to $CO_x$ species and $H_2O$ as well as dehydrogenation to $C_2H_4$, with the $C_2H_4$ product desorbing between 300 and 450 K. Both DFT calculations and TPRS experiments show that $C_2H_4$ desorption is the rate-limiting step in the conversion of $C_2H_6$ to $C_2H_4$ on $IrO_2(110)$ during TPRS. Our experimental results demonstrate that partially hydrogenating the $IrO_2(110)$ surface enhances the conversion of ethane to ethylene while suppressing ethane oxidation to $CO_x$ species. According to DFT, converting a fraction of the $O_{br}$ atoms to $HO_{br}$ groups causes $C_2H_4$ desorption to become favored over further dehydrogenation because $HO_{br}$ groups are poor H-atom acceptors compared to $O_{br}$ atoms. Our findings reveal that the $IrO_2(110)$ surface exhibits an unusual ability to promote the dehydrogenation of ethane to ethylene near room temperature during TPRS, and demonstrate that controlled deactivation of $O_{br}$ atoms is an effective way to promote ethylene production from ethane on $IrO_2(110)$.

REFERENCES

1. Gartner, C. A.; van Veen, A. C.; Lercher, J. A., "Oxidative dehydrogenation of ethane: Common principles and mechanistic aspects". *Chemcatchem* 2013, 5, 3196-3217.
2. Cavani, F.; Ballarini, N.; Cericola, A., "Oxidative dehydrogenation of ethane and propane: How far from commercial implementation?". *Catal. Today* 2007, 127, 113-131.
3. Banares, M. A., "Supported metal oxide and other catalysts for ethane conversion: a review". *Catal. Today* 1999, 51, 319-348.
4. Gartner, C. A.; van Veen, A. C.; Lercher, J. A., "Oxidative dehydrogenation of ethane on dynamically rearranging supported chloride catalysts". *J. Am. Chem. Soc.* 2014, 136, 12691-12701.
5. Argyle, M. D.; Chen, K. D.; Bell, A. T.; Iglesia, E., "Effect of catalyst structure on oxidative dehydrogenation of ethane and propane on alumina-supported vanadia". *J. Catal.* 2002, 208, 139-149.
6. Argyle, M. D.; Chen, K. D.; Bell, A. T.; Iglesia, E., "Ethane oxidative dehydrogenation pathways on vanadium oxide catalysts". *J. Phys. Chem. B* 2002, 106, 5421-5427.
7. Martinez-Huerta, M. V.; Gao, X.; Tian, H.; Wachs, I. E.; Fierro, J. L. G.; Banares, M. A., "Oxidative dehydrogenation of ethane to ethylene over alumina-supported vanadium oxide catalysts: Relationship between molecular structures and chemical reactivity". *Catal. Today* 2006, 118, 279-287.
8. Rozanska, X.; Fortrie, R.; Sauer, J., "Size-dependent catalytic activity of supported vanadium oxide species: Oxidative dehydrogenation of propane". *J. Am. Chem. Soc.* 2014, 136, 7751-7761.
9. Carrero, C. A.; Schloegl, R.; Wachs, I. E.; Schomaecker, R., "Critical literature review of the kinetics for the oxidative dehydrogenation of propane over well-defined supported vanadium oxide catalysts". *ACS Catal* 2014, 4, 3357-3380.
10. Liang, Z.; Li, T.; Kim, M.; Asthagiri, A.; Weaver, J. F., "Low-temperature activation of methane on the $IrO_2(110)$ surface". *Science* 2017, 356, 298-301.
11. Li, T.; Kim, M.; Liang, Z.; Asthagiri, A.; Weaver, J. F., "Dissociative chemisorption and oxidation of $H_2$ on the stoichiometric $IrO_2(110)$ surface". *Top. Catal.* 2017, DOI: 10.1007/s 11244-017-0877-y.
12. Blochl, P. E., "Projector augmented-wave method". *Phys. Rev. B* 1994, 50, 17953-17979.
13. Kresse, G., "Ab-initio molecular-dynamics for liquid-metals". *J. Non-Cryst. Solids* 1995, 193, 222-229.
14. Kresse, G.; Hafner, J., "Abinitio Hellmann-Feynman molecular-dynamics for liquid-metals". *J. Non-Cryst. Solids* 1993, 156, 956-960.
15. Perdew, J. P.; Burke, K.; Ernzerhof, M., "Generalized gradient approximation made simple". *Phys. Rev. Lett.* 1996, 77, 3865-3868.
16. Grimme, S.; Antony, J.; Ehrlich, S.; Krieg, H., "A consistent and accurate ab initio parametrization of density functional dispersion correction (DFT-D) for the 94 elements H—Pu". *J. Chem. Phys.* 2010, 132, 154104.
17. Weaver, J. F.; Hakanoglu, C.; Antony, A.; Asthagiri, A., "Alkane activation on crystalline metal oxide surfaces". *Chem. Soc. Rev.* 2014, 43, 7536-7547.
18. Li, T.; Kim, M.; Rai, R.; Liang, Z.; Asthagiri, A.; Weaver, J. F., "Adsorption of alkanes on stoichiometric and oxygen-rich $RuO_2(110)$". *Phys. Chem. Chem. Phys.* 2016, 18, 22647-22660.
19. Henkelman, G.; Uberuaga, B. P.; Jonsson, H., "A climbing image nudged elastic band method for finding saddle points and minimum energy paths". *J. Chem. Phys.* 2000, 113, 9901-9904.
20. Chen, L.; Smith, R. S.; Kay, B. D.; Dohnalek, Z., "Adsorption of small hydrocarbons on rutile $TiO_2(110)$". *Surf Sci.* 2016, 650, 83-92.
21. Tait, S. L.; Dohnalek, Z.; Campbell, C. T.; Kay, B. D., "n-alkanes on Pt(111) and on C(0001)/Pt(111): Chain length dependence of kinetic desorption parameters". *J. Chem. Phys.* 2006, 125, 234308.
22. Pham, T. L. M.; Nachimuthu, S.; Kuo, J. L.; Jiang, J. C., "A DFT study of ethane activation on $IrO_2(110)$ surface by precursor-mediated mechanism". *Appl. Catal., A* 2017, 541, 8-14.
23. Antony, A.; Asthagiri, A.; Weaver, J. F., "Pathways and kinetics of methane and ethane C—H bond cleavage on PdO(101)". *J. Chem. Phys.* 2013, 139, 104702: 1-12.
24. Antony, A.; Hakanoglu, C.; Asthagiri, A.; Weaver, J. F., "Dispersion-corrected density functional theory calculations of the molecular binding of n-alkanes on Pd(111) and PdO(101)". *J Chem. Phys.* 2012, 136, 054702.
25. Dai, G. L.; Liu, Z. P.; Wang, W. N.; Lu, J.; Fan, K. N., "Oxidative dehydrogenation of ethane over V2O5 (001): A periodic density functional theory study". *J. Phys. Chem. C* 2008, 112, 3719-3725.
26. Cheng, M. J.; Goddard, W. A., "In silico design of highly selective Mo—V—Te—Nb—O mixed metal oxide catalysts for ammoxidation and oxidative dehydrogenation of propane and ethane". *J. Am. Chem. Soc.* 2015, 137, 13224-13227.
27. Anic, K.; Bulchtiyarov, A. V.; Li, H.; Rameshan, C.; Rupprechter, G. *J. Phys. Chem. C* 2016, 120, 10838.
28. Arman, M. A.; Klein, A.; Ferstl, P.; Valookaran, A.; Gustafson, J.; Schulte, K.; Lundgren, E.; Heinz, K.; Schneider, A.; Mittendorfer, F.; Hanuner, L.; Knudsen, J. *Surf Sci.* 2017, 656, 66.
29. Kisters, G.; Chen, J. G.; Lehwald, S.; Ibach, H. *Surf Sci.* 1991, 245, 65.
30. Lerotholi, T. J.; Held, G.; King, D. A. *Surf Sci.* 2007, 601, 1285.
31. Li, T.; Kim, M.; Rai, R.; Liang, Z.; Asthagiri, A.; Weaver, J. F. *Phys. Chem. Chem. Phys.* 2016, 18, 22647.
32. Liang, Z.; Kim, M.; Li, T.; Rai, R.; Asthagiri, A.; Weaver, J. F. *J. Phys. Chem. C* 2017, 121, 20375.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

Embodiments of the present disclosure will employ, unless otherwise indicated, techniques of separating, testing, and constructing materials, which are within the skill of the art. Such techniques are explained fully in the literature.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

The invention claimed is:

1. A method of converting a base gas to a first gas, comprising:
exposing the base gas to an $IrO_2$-based catalyst, and forming the first gas,
wherein the base gas is an alkane, wherein the first gas comprises an alkene, an alkyne, an alcohol, an aldehyde, or a combination thereof;
wherein the $IrO_2$-based catalyst has the formula of $Ir_xM_yO_z$ or $Ir_xO_yX_z$ wherein M is selected from Ru, Ti, Re, Nb, Ta, Os, Pt, Pd, Cu, Ag, Au, Rh, Cr, Mn, Ni, Fe, Co, and a combination thereof, where X is selected from F, Cl, Br, I, S, Se, Te, and a combination thereof, wherein for $Ir_xM_yO_z$ y is greater than 0, z is between 1 and 2 and $x+y \leq 1$ and wherein for $Ir_xO_yX_z$ X is present and X is an element that replaces a fraction of the O-atoms in the anion sub-lattice, and wherein for $Ir_xO_yX_z$ $x \leq 1$ and y+z is between 1 and 2.

2. The method of claim 1, further comprising prehydrogenation of the $IrO_2$-based catalyst prior to exposing the alkane to the $IrO_2$-based catalyst; wherein prehydrogenation comprises adsorbing hydrogen onto a surface of the $IrO_2$-based catalyst to convert at least a portion of oxygen to OH.

3. The method of claim 1, wherein the alkane is a C1 to C5 alkane.

4. The method of claim 1, wherein the first gas comprises a C1 to C5 alkene, a C1 to C5 alkyne, a C1 to C5 alcohol, a C1 to C5 aldehyde, or a combination thereof.

5. The method of claim 1, wherein exposing comprises exposing the alkane to the $IrO_2$-based catalyst at a temperature of about 200 to 400 K.

6. The method of claim 1, wherein the $IrO_2$-based catalyst comprises $IrO_2$ deposited onto a support.

7. The method of claim 6, wherein the support is an oxide support selected from $SiO_2$, $Al_2O_3$, $TiO_2$, MgO, CaO, $CeO_2$, zeolites, and a combination thereof.

8. The method of claim 6, wherein the support is a non-oxide support.

9. The method of claim 1, wherein the base gas is ethane, and the first gas is ethylene.

10. The method of claim 1, wherein the base gas is methane and the first gas comprises ethylene, methanol, formaldehyde, or a combination thereof.

11. A method of converting a base gas to a first gas, comprising:
exposing the base gas to an $IrO_2$-based catalyst, and forming the first gas,
wherein the base gas is an alkane, wherein the first gas comprises an alkene, an alkyne, an alcohol, an aldehyde, or a combination thereof;
wherein the $IrO_2$-based catalyst has the formula of $Ir_xM_yO_z$ or $Ir_xO_yX_z$ wherein M is selected from Ru, Ti, Re, Nb, Ta, Os, Pt, Pd, Cu, Ag, Au, Rh, Cr, Mn, Ni, Fe, Co, and a combination thereof, where X is selected from F, Cl, Br, I, S, Se, Te, and a combination thereof, wherein for $Ir_xM_yO_z$ y is greater than 0, z is between 1 and 2 and $x+y \leq 1$ and wherein for $Ir_xO_yX_z$ $x \leq 1$ and y+z is between 1 and 2; and
prehydrogenation of the $IrO_2$-based catalyst prior to exposing the alkane to the $IrO_2$-based catalyst; wherein prehydrogenation comprises adsorbing hydrogen onto a surface of the $IrO_2$-based catalyst to convert at least a portion of oxygen to OH.

12. The method of claim 11, wherein the alkane is a C1 to C5 alkane.

13. The method of claim 11, wherein the first gas comprises a C1 to C5 alkene, a C1 to C5 alkyne, a C1 to C5 alcohol, a C1 to C5 aldehyde, or a combination thereof.

14. The method of claim 11, wherein exposing comprises exposing the alkane to the $IrO_2$-based catalyst at a temperature of about 200 to 400 K.

15. The method of claim 11, wherein the $IrO_2$-based catalyst comprises $IrO_2$ deposited onto a support.

16. The method of claim 15, wherein the support is an oxide support selected from $SiO_2$, $Al_2O_3$, $TiO_2$, MgO, CaO, $CeO_2$, zeolites, and a combination thereof.

17. The method of claim 15, wherein the support is a non-oxide support.

18. The method of claim 11, wherein the base gas is ethane, and the first gas is ethylene.

19. The method of claim 11, wherein the base gas is methane and the first gas comprises ethylene, methanol, formaldehyde, or a combination thereof.

* * * * *